United States Patent
Lefebvre et al.

(10) Patent No.: US 6,175,060 B1
(45) Date of Patent: *Jan. 16, 2001

(54) PHOSPHATE-DEFICIENCY INDUCIBLE PROMOTER

(75) Inventors: Daniel D. Lefebvre, Kingston (CA); Mohammad A. Malboobi, Qom (IR)

(73) Assignee: Performance Plants, Inc., Kingston (CA)

( * ) Notice: Under 35 U.S.C. 154(b), the term of this patent shall be extended for 0 days.

This patent is subject to a terminal disclaimer.

(21) Appl. No.: 09/299,450

(22) Filed: Apr. 26, 1999

Related U.S. Application Data

(63) Continuation of application No. 08/804,794, filed on Feb. 24, 1997, now Pat. No. 5,922,564.

(51) Int. Cl.[7] .............................. C12P 22/00; A01H 3/00; A01H 15/05; C12N 1/19
(52) U.S. Cl. ........................ 800/295; 800/278; 435/419; 435/69.1
(58) Field of Search .................................. 435/69.1, 91.4, 435/468, 455, 421, 410, 418, 419, 430, 320.1; 800/250, 295, 278; 424/132.1; 426/629

(56) References Cited

U.S. PATENT DOCUMENTS 5,922,564   7/1999   Lefebvre et al. .................... 435/69.1

FOREIGN PATENT DOCUMENTS

| 9252782A | 9/1997 | (JP) . |
|---|---|---|
| WO9804701 | 2/1998 | (WO) . |
| WO9805760 | 2/1998 | (WO) . |

OTHER PUBLICATIONS

Okumura, A et al., "*Arabidopsis thaliana* gene for phosphate transporter," EMBL Database, Acc. No. E13983, Jun. 23, 1998.
Malboobi, M.A., Lefebvre, D.D., (1995) *Plant Mol. Biol.* 28:859–870.
Malboobi, M.A., Tremblay, L., Lefebvre, D.D., (1996) Identification and Nucleotide Sequences of cDNA Clones of Phosphate–Starvation inducible β–Glucosidase Genes of Brassicaceae (Accession Nos. U72153 and U72154). (PGR96–114) *Plant Physiol.* 112:139.
Nakao, J.,et al. (1986) *Mol Cell. Biol.* 6:2613–2623.
Sadka, A., et al. (1994) *Plant Cell* 6:737–749.
Venter, U., et al. (1994) *EMBO J..* 13:4848–4855.
Vogel, K., et al. (1989) *Mol. Cell Biol.* 9:2050–2057.
Arndt, K.T., et al. (1987) *Science* 237:874–880.
Rudolph, H. and Hinnen, A. (1987) *Proc. Natl. Acad. Sci. USA* 84:1340–1344.
Svaren, J., et al. (1989) *EMBO J..* 13:4856–4862.
Fascher, K.D., et al. (1990) *EMBO J.* 9:2523–2528.
Klein, C. and Struhl, K. (1994) *Science* 266:280–282.
Malboobi, M.A. et al. (1997) *Plant Mol. Biol.* 34(1): 57–68.
Lui, Chunming, et al. (1996) *Plant Mol. Biol.,* 33:867–874.

Primary Examiner—Robert A. Schwartzman
Assistant Examiner—Katharine F Davis
(74) Attorney, Agent, or Firm—Hamilton, Brook, Smith & Reynolds, P.C.

(57) ABSTRACT

This invention provides an isolated promoter which induces transcription of a gene under conditions in which phosphate is limited to an organism. Vectors, host cells, and transgenic photosynthetic organisms incorporating this promoter are also provided.

29 Claims, 12 Drawing Sheets

```
AAAAACATGT TATTTTAAAT TTCCAATTTT ACTTTTCAAA TAAACTTCCA CGTTTATTCT    -1640

TTAATTTAAT TATTCAATTT GTTTAAATTA ACACTCACTC TGATCATTAT ATAGGATATT    -1580

TCAGAGATTT ATTTAGGATG TTTTACTAAT ATCAATGCAA TTTTTAAATA TATTTTATTT    -1520

GATTATTTGA CTATTGGGTT TGTATTTTGT ATTTTAATA TCAAGAGAAC AAATTTTATA     -1460

ATTAAAAATA AATTTCTTAA AGTGTGTGTT TTAATCTAAA ACATCATATA ATTTGAAATA    -1400

GAGGAAATAT CATCTAATAA AGTAATGTAT ATTTGTATAG TTAATGATTT GTCTTTTTAT    -1340

TCGCGCAAAA TGTGTCAATT ATAAAATATA AAGAGGATAT AATTTAGTTT AGAGTTTTAG    -1280

ACACGAGGAC TATATATTGG AAAACAAAAA AGTAATGTAA ACCATATAGA TCATGGAATG    -1220

AGTCATCCTA TTAAACAGTT GTATTATATA TTTATATTTT AGTCACTAAC ACATTAATAA   -1160

CTTAACGTCC ATAACAAAAT AAGATCCAAA ACTCGATCTA GATCTATACG AGGCACTAAA   -1100

TGATCCATTG ACTTAGGGCC GGCCGATTGG TTCGAGGACT CCTCATGCTG TAAACTTTTT   -1040

TTTTGGACAT ACATGATATA TTTTTAAGTC ACGTTTTTAT ATTATATGTT CCACGCCCAA    -980
                                                ⌐         ⌐
                              ±R  +R
                  -R        ⌐     ⌐        ⌐

TATAATATGT TCCAAACTAG GAAAAATAAG TAAGAATTAG TCAATGATCG AGATAATGCA     -920
⌐                                       ⌐           ⌐      -R
          -R                      +R           +R    ⌐
                 -R                     ⌐

ATGAATCATC CTATTTATTA AATAGATTTA CTAAACTATA TATAATACAA TGATCGAGAT     -860
⌐                                                      ⌐         ⌐
           -R                                                 +R   -R
                     -R

CGTGCCATGA AGCATCCTAT ATACTATAAA AATAGTCTTA CTAAATACAT ACTCATATAG     -800
                                -R

TTTAGTCATT CATTAGTCCA AACATTAAAT GAGAGATCCT TTACTTGCTA CCTGAATTTT     -740
          -R

TTCAGAATAA GGTATAACTT TTTTTCGAAT TAGAAACTGA TTTATGAAAG ATTAAGAGTA    -680

ATGTTCGTTA AACAAGTTAA AAAATATGTT TTTACAATTA AGTTTTGAAA AATAATAAAG    -620
                ±R
TCTCCAATTA TTTGAGTATC AAAAATAGGC TTGTTATTAT TTAGGGTTTT CGTTGGTTTA    -560
          ±R                           ±R

AATGCAACGG GGTGTGGTTG TCATTGTGGA AGTTAATGGA AGTAATTGGT TGAGGTTTTA    -500
                                                     +R
```

FIGURE 2A

```
AACGTTATCG GACATTTTAA ATGACTGGTT TACAGTTAAA AATATGTGTA TTTACGGCAA    -440
                         └──+R──┘
TTTTATGATT GGCTTAGCAG TAGATGCGAC AGTGGTTTAA ACCAAAAATT ACCAAATAAA    -380
    └──+R──┘                                          └──±R──┘
└────±R────┘                         ┌────±R─────┐
TAATATACAA TTATTAAATT ATATAAAACA CCAATATTAT ATATTTATAT ATATATGAAC    -320
         └────±R────┘                 └────±R────┘
                                                ┌──
ATAGTTAATT ATCGAAACCA TAGACAAAGT ACATAAGAGT TATTCCGAAA AAGGTTTATT    -260
                                         └──±R──┘
└──±R──┘                  ┌────±R────┐           ┌─────
ATGAAACACA AATAATCATA TTGGGAGATT ATGATATCCA AAATGGACTA ATCAAATAAT    -200
         └────±R────┘                                    └──-R──┘
 ──-R──┐                       ┌──-R──┐
TAAATCCAAA ATGGATGAAG AACTTATATT AGTTCCACGC ACAATATAAT ATGTTCCAAA    -140
                               └──-R──┘                 +R   ±R
     -R                   +R
CTAAGTAAGA ACACAACGGT CGAGGTCATG CAATGAATCA TCCTATATAT AAAATAGTTT    -80
 -R       -R         +R                   -R            +R
┐
TACTAAACAA TTATATTTTA GTCACTCGTT AACAAACAAT CAAAATCGCT ATATAAAGAA    -20
 -R      +R                           -R      TATA box
CTCCGATTGG ATGTAAACAA ATCATCATAA ACTTGTTCTC TTCCAGAAGA AACTAAAAAC     41
         +1
AAAAATGGCA TTGCAAAAGT TTCCTCTCAT GGGGCTGCTT TTGCTCCTAA CCATCCTCGT    101
CTCTGTGACA ACAGCGGTTG ATGATCCTGT TTGCCCGGCG ACTTCCAAGC TAAGCCGAGC    161
AAGTTTCCCT AATGGGTTTT TGTTTGGCAC GGCTACTGCT GCGTTTCAGG TACAACAGAT    221
TTACTAAATC ATAGTTCAAA AAACAAAAAG TAGTGTCGTT ATTGTGTTTC TATCTGAATT    281
```

FIGURE 2B

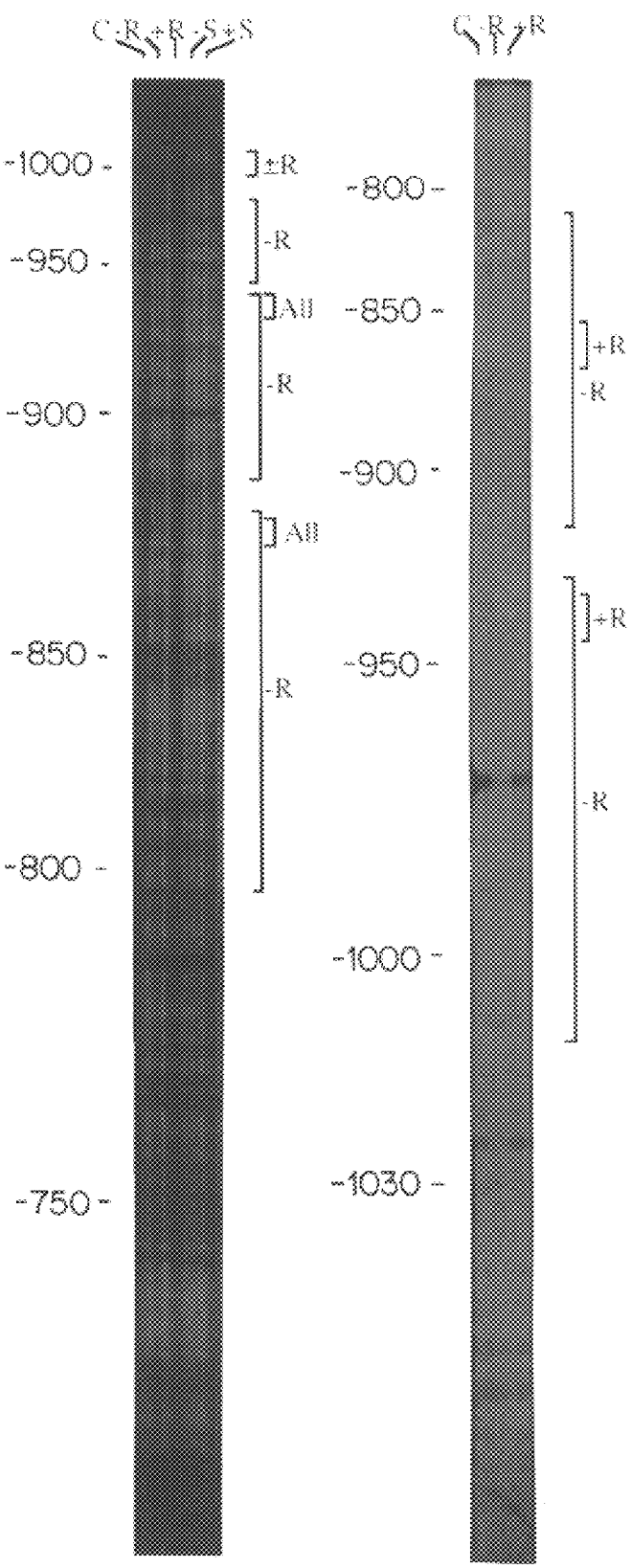

```
-173 tattAGTTCCACGCACAATATATAATATATGTTCCAAACTAAGTAAGAacaCAACGGTCGAGGTCAtgc
     ataaTCAAGGTGCGTGTTATATTATACAAGGTTTGATTCATTCttgtGTTGcCAGCTCCAGTacg
              BOX III                                         BOX II
```

```
     aatgaATCATCCTATATATAAAATAGtttactaaac -70
     ttactTAGTAGGATATATATTTTATCaaaatgatttg
              BOX I
```

FIG. 7A

P$_i$-Starved Root
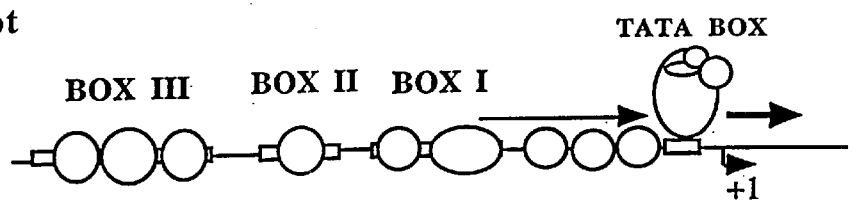
P$_i$-Fed Root
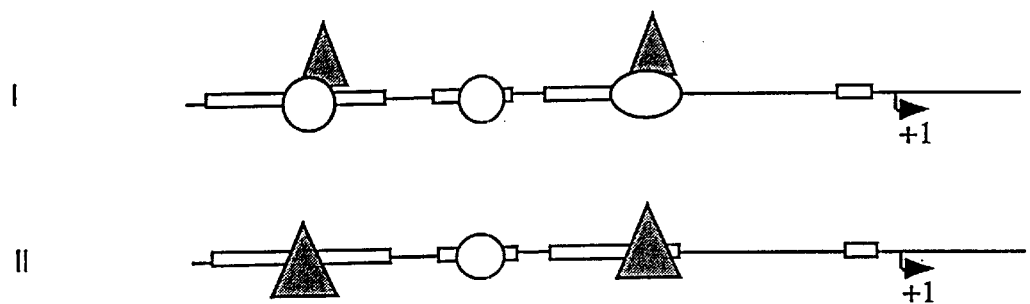
FIGURE 9

PHOSPHATE-DEFICIENCY INDUCIBLE PROMOTER

RELATED APPLICATIONS

This application is a continuation of 08/804,794, filed Feb. 24, 1997, now U.S. Pat. No. 5,922,564, the entire teachings of which are incorporated herein by reference.

BACKGROUND OF THE INVENTION

Phosphorus is one of the most important nutrients for plants, being essential for their growth and a structural component of nucleic acids, phospholipids, intermediary metabolites and numerous other biological molecules. In plants, the only readily absorbed form of exogenous phosphorus is inorganic phosphate ($P_i$) (Bieleski, 1973). When the amount of available phosphate is low, plants are unable to grow vigorously and productively. When phosphate is absent, growth is halted and the plant dies.

The phosphate to nitrogen ratio in plants affects both the temporal and quantitative characteristics of flowering (Salisbury and Ross, 1985). Relatively high phosphate advances maturity in plants, whereas relatively low phosphate results in little or no flowering taking place. Phosphate levels are also known to affect the biomass ratio between root and shoot. Specifically, phosphate deprivation causes preferential growth of roots (Lefebvre et al., 1982). Thus, in many environments, the availability of phosphorus becomes a major factor limiting the growth and reproduction of photosynthetic organisms.

Plants and other photosynthetic organisms are either sessile or restricted in movement and therefore limited in nutrient availability to their immediate environment. As a result, photosynthetic organisms require signal transduction pathways in order to trigger cellular responses to adverse environmental stimuli. As part of the adenosine nucleotides, ADP and ATP, which are the currency of cellular energy, phosphorus is critical to bioenergetics. The covalent addition or removal of a phosphate group to or from a biological substrate (phosphorylation and dephosphorylation, respectively) often functions as a kind of regulatory "on/off switch" in cellular metabolism and signal transduction. For example, the phosphorylation and dephosphorylation of certain membrane-bound receptor protein kinases and their substrates are key to various signal transduction pathways, including pathways of plant hormones such as ethylene (Kieber et al., 1993) and abscisic acid (Anderberg and Walker-Simmons, 1992). Self-incompatibility with respect to pollination and fertilization also involves the activity of protein kinases encoded by S-locus genes (Tantikanjana et al., 1993; Zhang and Walker, 1993). Regulatory signals can also trigger mechanisms for disease and pest control.

Although the nature of the phosphate-starvation response has been investigated in plants, little is known of the molecular mechanisms that regulate phosphorus uptake and metabolism. Few genes associated with phosphate-starvation expression in plants have been identified and isolated. To date, no reports of promoters which specifically respond to phosphate-starvation conditions are known.

Among the promoter sequences available for the genetic engineering of plants, depending upon the transcription initiation characteristics desired, (strength, tissue specificity, developmental specificity, etc.), different promoters can be employed to initiate transcription of a DNA sequence of interest joined at the 3' end of the promoter region. For example, promoters such as the 35S Cauliflower Mosaic Virus (CaMV 35S), mannopine synthase (mas) and octopine synthase (ocs) have been used successfully to direct the expression of desired nucleic acid sequences in transformed plant tissue. When expressed in a transgenic plant, DNA sequences under the control of these promoters are found at relatively low or moderate levels and are expressed fairly evenly (i.e. constitutively) throughout the plant. See, for example, van der Zaal, et al. (1991) *Plant Mol. Biol.* 16:983; Ohl, et al. (1990) *Cell* 2:837.

Of particular interest, however, are promoters which demonstrate enhanced transcription initiation characteristics in rapidly dividing cells or rapidly growing tissue, against stress or other detrimental factors. Likewise, there are advantages with the increased expression of a DNA sequence of interest under the regulation of an inducible promoter. Such promoters regulate the expression of genes in response to environmental factors, such as light, wounding, exposure to heavy metals, low nutrient status, and/or temperature. However, isolated DNA elements responsive to environmental nutrients are rare.

The discovery of new promoters with useful transcript initiation patterns, especially ones having very strong promoter activity, are essential for the controlled expression of desirable nucleic acid sequences. Promoters which show enhanced activity induced by environmental phenomena are also of special interest for many genetic engineering tools to enhance plant characteristics generally, as these critical gene sequences are abundant in young or stressed plant tissue. Thus, a need exists for promoter sequences which can be used in recombinant DNA constructions to enable the external control of the expression of genes which can confer agronomic advantages when expressed at the proper time.

SUMMARY OF THE INVENTION

This invention provides a regulatory sequence useful for genetic engineering of plant cells to provide a method of controlling the timing or tissue pattern of expression of DNA sequences linked to this novel regulatory sequence.

This invention further relates to the 5'-flanking region (promoter) of a phosphate-starvation responsive β-glucosidase gene from *Arabidopsis thaliana* and to the regulatory-protein-binding sites within the 5'-flanking region of the phosphate-starvation responsive gene.

This invention also relates to manipulation of structure and the use of this promoter, or truncated sequences located within the promoter, to control, by the limitation of phosphate, the expression of genes in higher plants and other photosynthetic organisms.

The invention further provides a plant promoter that is capable of directing the expression of a gene of interest in specific tissues or throughout the body of a photosynthetic organism. In a preferred embodiment, the promoter is used to direct expression of a gene in a cell or tissue of a plant.

In another aspect of this invention, a transformation or an expression vector is provided comprising a promoter according to this invention. The promoter can be fused to a gene of interest and introduced into a photosynthetic organism, preferably a plant, to produce a product.

Further, this invention provides a transformed cell of a plant or another photosynthetic organism incorporating an isolated or recombinant promoter or functional fragment thereof in combination with a gene of interest of which the promoter directs expression.

Transgenic plants and other photosynthetic organisms are also provided which contain the constructs of this invention. In one embodiment, a transgenic plant is provided with a promoter according to this invention fused to a psr3.2 gene. Cultured cells and tissue derived from plants or other photosynthetic organisms which contain the nucleic acid constructs of this invention are also provided herein. This includes antisense constructs comprising the promoter of this invention linked to antisense nucleic acid which encodes a product expressed through the activity of an endogenous phosphate-deficient inducible promoter.

This invention further provides methods to alter the response of a cell, tissue, plant part or a plant or other photosynthetic organism to conditions under which phosphate is limiting. The promoter and methods of this invention can be used to selectively express structural genes in plants, especially in roots and shoots. The methods comprise growing a plant having integrated into its genome a regulatory region, or functional portion thereof, provided by this invention, operably linked to a structural gene.

This invention further provides a means for generally or specifically conferring resistance to pathogenic organisms or diseases in a plant which is most susceptible to such a pathogenic organism or disease under conditions of phosphate starvation. This use can result in the minimization or elimination of externally applied chemical treatments to control such pests or diseases.

BRIEF DESCRIPTION OF THE FIGURES

FIGS. 2A–2B. DNA sequence of 5'-flanking region of psr3.2 gene (SEQ ID NO:1) and a summary of in vitro DNase I footprinting and in vivo DMS-footprinting results. The putative transcription (+1) and translation start sites (underlined) are indicated. Dark and light overlapped arrows show the major and the minor transcription start sites, respectively. The results of in vitro DNase I footprinting experiments presented in FIG. 5 and FIG. 6 are summarized here. Brackets above and below the sequence encompass the in vitro DNase I protected regions as revealed by labeling the 3'-end of the top or bottom strands of the DNA. The binding sites for proteins extracted from $P_i$-starved roots ($-R$), from $P_i$-fed roots ($+R$), from both types of roots ($\pm R$) or from roots and shoots (all) are illustrated. The squared and circled nucleotides are the ones with enhanced or suppressed in vivo dimethyl sulfate (DMS) modifications, respectively, as shown in FIG. 8. The 5' flanking region and a portion of the 5' end of the DNA sequence encoding psr3.2 protein are shown (SEQ ID NO:2).

FIGS. 6A–6D. Autoradiograms of in vitro DNase I footprinting of the homologous regions. DNA probes (FIG. 5) were incubated with proteins extracted from the $P_i$-starved root ($-R$) and shoots ($-S$) and the $P_i$-fed roots ($+R$) and shoots ($+S$). A control reaction (6C) contained only probes and the buffer was run in parallel. After 20 min of incubation at room temperature in 55 mM salt solution, all samples were treated with DNase I for 60 sec. Partially digested DNA fragments were purified and separated through a denaturing-polyacrylamide gel. Autoradiograms on the left (6A and 6B) display footprinting of the region proximal to the TATA box and the ones on the right (6C and 6D) are footprinting of the distal regions. DNase I protection assays with shoot protein extracts were done only for the bottom strands (6A and 6C) but not for the top strands (6C and 6D). Brackets indicate the protected regions by proteins extracted from $P_i$-starved roots ($-R$), from $P_i$-fed roots ($+R$), from both types of $P_i$ treatments of roots ($\pm R$) or from roots and shoots (all) as compared to the control lane.

FIGS. 7A–7B. Results of electrophoresis mobility shift assays of synthetic oligonucleotides. Double-stranded oligonucleotides corresponding to the sequences within the homologous boxes (FIG. 3) were labelled with $T_4$ polynucleotide kinase in the presence of $[\gamma^{32}P]$-dATP. The labelled probes were exposed to protein extracts and loaded onto a native gel as described in FIG. 4. The sequences of each oligonucleotide is shown by capital letters on the top (7A) of each assay (7B). The shifted bands are indicated by arrows.

FIG. 9. A diagrammatic illustration of the regulatory protein binding and gene expression induction in response to $P_i$ starvation. Upon sensing the limitation of $P_i$, activators (open circles) bind to their cognate sites within the boxes and induce the expression of psr genes through interaction with the transcription initiation complex. In contrast, when there is sufficient $P_i$ in the medium, repressors (shaded triangles) bind and cause reduction or inhibition of gene expression either by binding to the activators (I) or the DNA (II).

DETAILED DESCRIPTION OF THE INVENTION

Figure 1:
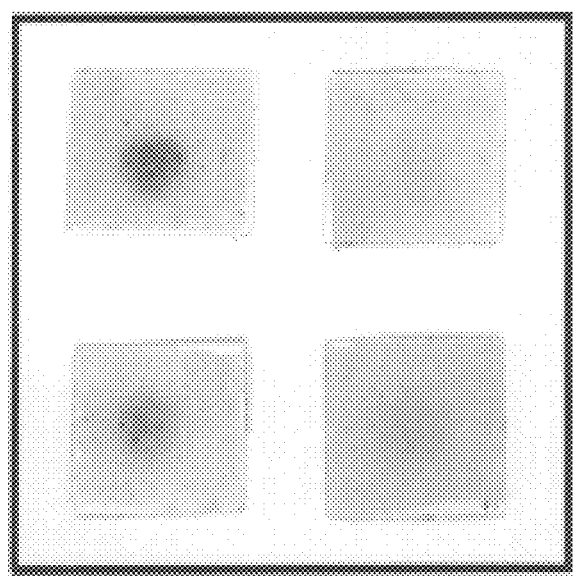
FIG. 1. Detection of concentrations of psr3 nuclear runoff products from $P_i$-starved ($-P_i$) and $P_i$-fed ($+P_i$) *A. thaliana* roots.

This invention provides isolated and/or recombinant nucleic acids, especially DNA, which, under conditions wherein phosphate is limiting, or under other conditions of stress (such as disease, insect or nematode attack), to a cell of a plant or another photosynthetic organism, can initiate transcription of another DNA sequence. By "limiting", it is meant that the level of phosphate uptake is below that required for the immediate requirements of a plant or photosynthetic organism. The term "starvation" refers to a level of phosphate available to the plant which is not only limiting, but is below that required for normal maintenance and/or growth wherein, if phosphate is maintained at that level, the plant or photosynthetic organism would eventually die for lack of adequate phosphorus. Limiting or starvation levels of phosphate result in a phosphate deficiency which causes the promoter provided by this invention, to activate transcription of a structural gene operably linked to the promoter. When phosphate levels are sufficient, the promoter is inactivated through the binding of repressor molecules.

A structural gene, in the context of this invention, is a gene, regulatory or otherwise, which encodes a product, such as a peptide, polypeptide or protein. This includes substances which are endogenous to the cell or tissue wherein the gene is expressed. Or, alternatively, foreign products can be expressed for purposes such as insect or disease resistance, altered products in flowers, seeds or fruits, or in vegetative pails of a photosynthetic organism. Expression of human and animal products can also be produced and controlled in transgenic cells and tissues through the use of the promoters of this invention. Those of skill in the art will recognize that these examples are not limiting and a wide array of substances can be expressed through application of the constructs and methods of this invention.

More specifically, this invention provides a regulatory region (SEQ ID NO:1) located 5' of a phosphate-starvation responsive β-glucosidase gene from *Arabidopsis thaliana*. This regulatory region consisting of residues −1700 to −20 (1680 nucleotides) of FIGS. 2A–2B initiates transcription of the phosphate-starvation responsive gene psr3.2 of *A. thaliana* (Malboobi, Tremblay and Lefebvre (1996)) and can be used to induce transcription of a gene to which it is fused at the 3' end.

Accordingly, in one aspect of this invention, a method is provided for producing a gene product under the control of a phosphate-deficiency inducible promoter by expressing a gene encoding the gene product in the cell of a plant or other photosynthetic organism comprising the steps of: transforming a plant cell with a DNA construct comprising a) a phosphate-deficiency inducible regulatory region (such as SEQ ID NO:1 or a functional portion thereof), DNA comprising a structural gene encoding a gene product, and a 3' untranslated region containing a polyadenylated region; regenerating a plant, photosynthetic organism or tissue culture from the cell; and placing the plant, photosynthetic organisms or tissue culture under conditions of phosphate deficiency so that the promoter induces transcription of the structural gene and the gene product is expressed.

In the context of this disclosure, the terms "regulatory region" or "promoter" refer to a sequence of DNA, usually upstream (5') to the coding sequence of a structural gene, which controls the expression of the coding region by providing recognition and binding sites for RNA polymerase and/or other factors required for transcription to start at the correct site. The term "functional portion" or "functional fragment" refers to a truncated sequence of a promoter (of this invention) which maintains the capability of inducing transcription of a structural gene under the phosphate deficient conditions as described supra.

The constructs and methods described herein can be applied to all types of plants and other photosynthetic organisms, including: angiosperms (monocots and dicots), gymnosperms, spore-bearing or vegetatively-reproducing plants and the algae, including the cyanophyta (blue-green algae). Particularly preferred plants are those plants which provide commercially-valuable crops, such as corn, wheat, cotton, rice, canola, sunflowers, potatoes, tomatoes, carrots, and the like.

Further, the constructs and methods of this invention can be adapted to any plant part, protoplast, or tissue culture wherein the tissue is derived from a photosynthetic organism. The term "plant part" is meant to include a portion of a plant capable of producing a regenerated plant. Preferable plant parts include roots and shoots and meristematic portions thereof. Other plant parts encompassed by this invention are: leaves, flowers, seeds, epicotyls, hypocotyls, cotyledons, cotyledonary nodes, explants, pollen, ovules, meristematic or embryonic tissue, protoplasts, and the like. Transgenic plants can be regenerated from any of these plant parts, from tissue culture, or from explants. Methods will vary according to the species of plant.

Isolation and Characterization of Regulatory Region

This invention relates to the characterization and isolation of the 5' regulatory region of a phosphate-starvation responsive β-glucosidase gene, psr3.2, from *Araeiidopsis thaliana*. Expression of the β-glucosidase gene psr3.2 is induced at the mRNA synthesis level in response to $P_i$ starvation as shown by nuclear run-off experiments (FIG. 1). When $P_i$-starved roots and $P_i$-sufficient roots were compared (FIG. 6A), psr3.2 TATA box protection from DNase I was only detected in $P_i$-starved roots. During induction of transcription, trans-activators seem to stabilize the interaction between the TATA box and the transcription initiation complex (Klein and Struhl, 1994).

Figure 3:
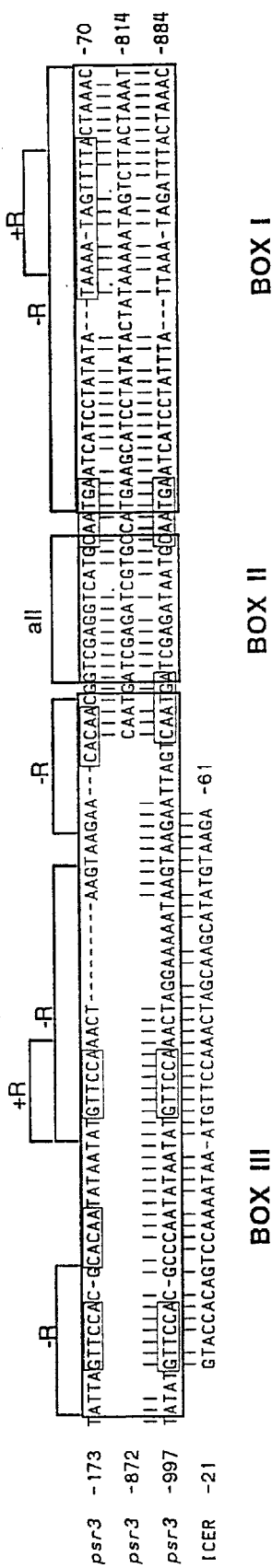
FIG. 3. Alignments of three homologous regions of psr3 promoter with each other and with ICER promoter. Numbers on both sides indicate the position of each segment. Vertical lines show the identical nucleotides among all sequences while dots (.) represent partially conserved residues. Based on the homology and DNase I protection patterns, three boxes can be defined (gray boxes). Brackets on the top show the DNase I protected regions of the homologous segment proximal to the TATA box. Symbols are as FIG. 2. These repeated sequences within these regions are enclosed in small rectangles.

As an initial step toward promoter analysis, the nucleotide sequence of more than 2000 bp upstream from the transcription start site was determined. There is a sequence homologous to the consensus TATA box sequence (TATATA[T/A][T/A]) centered at position −26 to −30 (FIG. 2B). In general, the sequence is extremely AT-rich (73%) with repeated A and T polynucleotides or AT dinucleotides. There are repeated CACAA sequences in the psr3.2 promoter region (FIG. 3). Deletion studies in yeast have indicated that this could be a PHO4-type binding site. (A PHO-type binding site is a regulatory site where transcription factors, either activators or repressors bind in bacteria and yeasts.) However, later work showed that the actual PHO4 binding sites in yeast similar to those described by Nakao et al, 1986 and Bergman et al, (1986) are located nearby and that these repeated sequences contribute only weakly to $P_i$-starvation induction (Rudolph and Hinnen, 1987). In vivo and in vitro footprinting experiments defined the precise yeast PHO4 binding sites which include a CACGT motif shared between both sites as described in Vogel et al, (1989). Such motifs are also present in the psr3 promoter region, but are not located in the DNase I protected regions.

Since trans-acting regulatory proteins usually have more than one binding site, the DNA sequence was searched for repeated motifs. Many sequences were found to be repeated two or more times including 18 direct and 24 inverse repeats longer than 10 bp in length. Noticeably, an AAACAA motif was repeated 15 times, of which 7 repeats occurred within the RNA sequence (once in 5'-UTR, exon-1, intron-6 and 3'-UTR, and twice in intron 4 and 6). Three segments of the DNA sequence located 641 bp apart were strongly homologous to each other (FIG. 3). The one proximal to the TATA box is located between position −173 to −70 and the other two are located next to each other between position −872 to −814 and between −997 to −884.

Figure 4A:
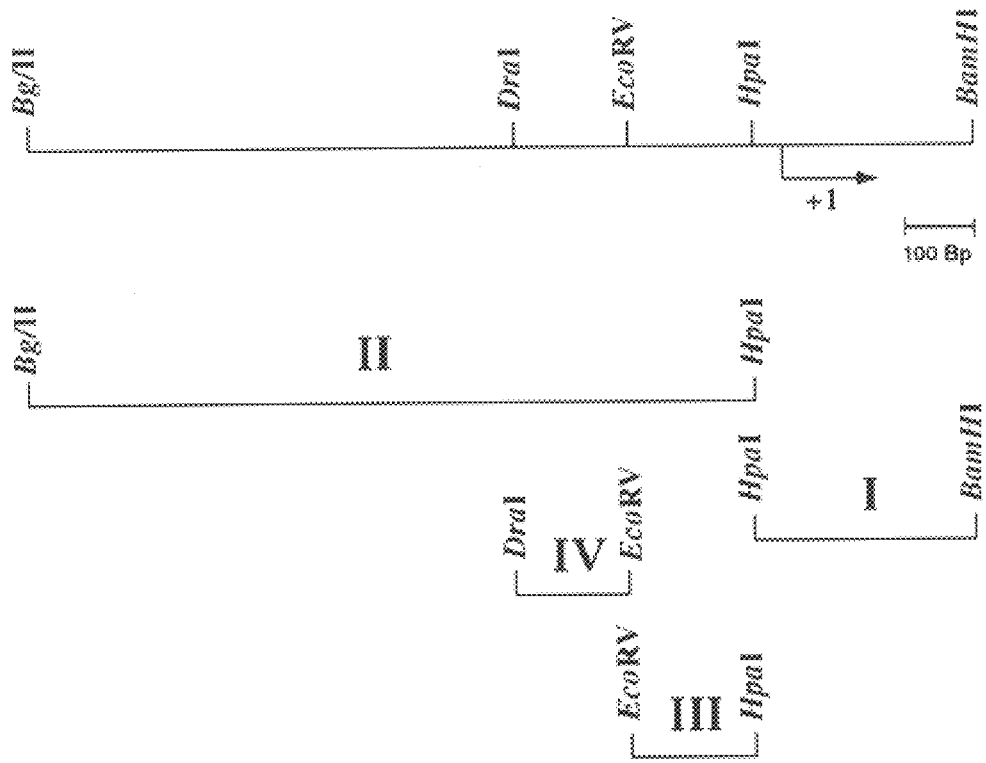
FIGS. 4A–4B. Results of electrophoresis mobility shift assays of restriction DNA fragments. DNA located between position −1120 to +282 was double digested by restriction enzymes (4A) and labelled either by the Klenow fragment of DNA polymerase I (fragment I and II) or $T_4$ polynucleotide kinase (fragment III and IV). Free DNA fragments and DNA fragments incubated with proteins extracted from the $P_i$-starved ($-R$) or the $P_i$-fed ($+R$) roots were resolved on a native polyacrylamide gel (4B). The shifted bands are indicated by arrows.
Figure 4B:
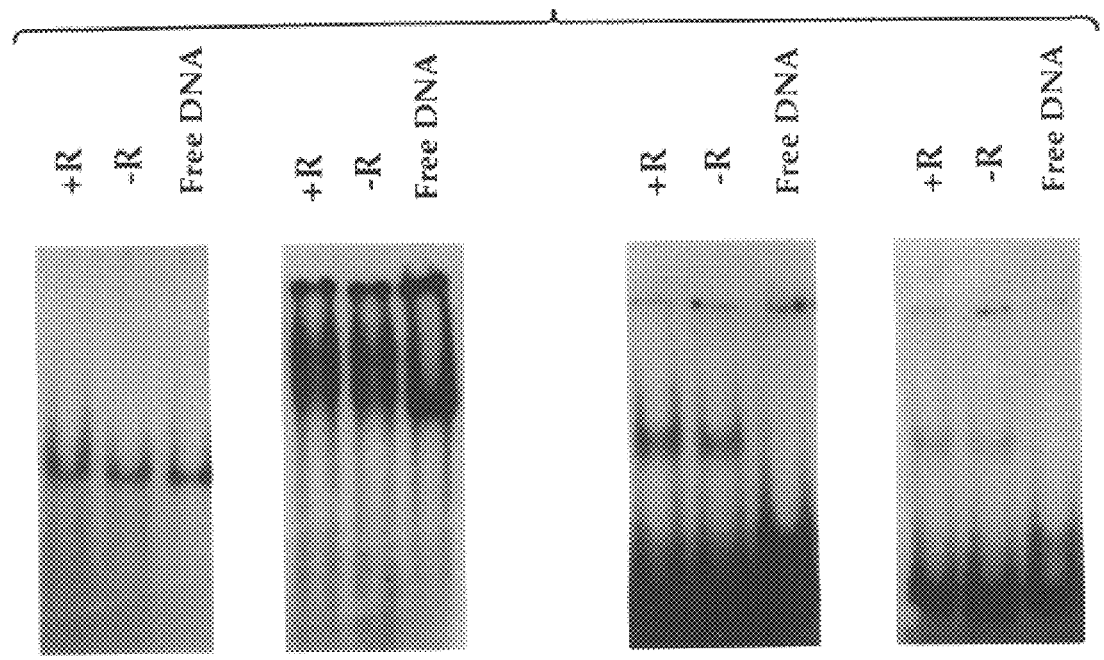

The upstream sequence of psr3.2 was investigated for possible protein binding sites by electrophoresis mobility shift assays (EMSA) and DNase I digestion protection assays. Initially, small scale preparation of crude nuclear protein extracts was used for EMSAs. The nuclear protein extraction method was adopted from the one developed by Dercker and Gannon (1994) for animal cell proteins. The optimized reaction solution contained one mg sheared herring sperm DNA (as non-specific competitor) per 50 mg of the protein extracts and 55 mM salt for both EMSA and footprinting experiments. Primarily, two DNA fragments were used for EMSA; one spans from the TATA box to the exon-1 and part of intron-1 (position −49 to +282; fragment I) and the other contained the promoter region (position −818 to −49; fragment II) (FIG. 4A). The $^{32}$P-labelled DNA fragments were incubated at room temperature with proteins extracted from $P_i$-fed and $P_i$-starved roots for 14 days. Assuming that protein-DNA complexes have slower electrophoretic mobility than the free DNA molecules, the above mixtures were resolved on a non-denaturing polyacrylamide gel. As shown in FIG. 4B, no shifted band was detectable for fragment I, while fragment II was shifted twice as a result forming complexes with factors present in both types of protein extracts. Two DNA fragments located within fragment II (FIG. 4A) were also subjected to EMSA. Both labelled HpaI-EcoRV (−224 to −50; fragment III) and EcoRV-DraI (−402 to −224; fragment IV) digestion products appeared to bind with the regulatory proteins. Closer examination of the autoradiogram indicated that DNA fragments complexed with proteins extracted from $P_i$-starved roots have slightly faster mobility than those bound to proteins derived from $P_i$-fed roots (FIG. 4B).

The above regions were scanned by footprinting to determine the locations and the number of protein binding sites. Several DNA fragments (FIG. 5) labelled at one 5'-end were incubated with crude whole cell extracts and partially digested by DNase I endonuclease. Separation of the digestion products on a denaturing polyacrylamide gel displayed where the DNA fragments were protected from the DNase I digestion by DNA-binding proteins. Again, no binding site was found within the 5' end of the structural gene. A region, 150-bp in length, ending at the TATA box was found to be protected by the DNA-binding proteins of the $P_i$-starved roots (FIGS. 6A and 6B). This region can be subdivided into several binding sites. Some are exclusively protected from digestion by $P_i$-starved root proteins while others are protected by both types of protein extracts. This 150 bp region coincides with the homologous segment of DNA proximal to the TATA box (FIG. 2). A second lengthy region protected by $P_i$-starved root proteins (FIGS. 6C and 6D) was found that also corresponds to the other two homologous segments of the upstream sequence (FIG. 2). Besides the strong homologies at the protein binding sites and similar pattern of protection, the binding sites coincide with the repeated sequences within the regions. Based on these criteria, three boxes can be distinguished (FIG. 3). The proximal and the distal segments contain all three boxes whereas the middle segment (next to the distal one) lacks box III. Box I, at the right hand side of each segments is fully protected by $P_i$-starved root proteins. This box contains a palindrome-like sequence (TAAAATAGTTTTTA) that is protected by all root and shoot protein extracts (FIGS. 6A and 6C). A repeated CAATGAA sequence at the junction of box I and II is also present in the box II and box III junction. Box II is shorter and less conserved than the other boxes. The sequence within this box interacted with both protein extracts of $P_i$-fed and $P_i$-starved roots as revealed by footprinting experiments. This box carries a dyad symmetrical sequence (GGTCGAGGTC) in the segment proximal to the TATA box. Box III contains a GTTCCA repeated sequence protected by $P_i$-starved root proteins. This repeat is adjacent to another repeated sequence, CACAA, (FIG. 3) which is also found in the core of a repeated sequence (CTGCACAA [A/T]G) within the PHO5 promoter region (Nakao et al, 1986; Bergman et al, 1986). One of the GTTCCA sequences was protected by $P_i$-fed derived proteins as well. However, the protection by $P_i$-starved protein extracts covered longer stretches of DNA that include the GTTCCA repeats and its neighbor sequences. Box III is homologous to a 48 bp sequence at the promoter of an inducible cAMP early repressor (ICER) gene. Several other protein binding sites for proteins extracted from both $P_i$-fed and $P_i$-starved roots were scattered between the two homologous segments (FIG. 2). These sites are both AT-rich and could represent the binding sites for general transcription factors or the factors which determine tissue specificity. A DNA sequence located between position −322 and −310 was also found to be similar to a conserved region between PH05 and HIS4 promoters in yeast (Arndt et al, 1987). This sequence was not protected in the psr3 promoter nor in the PHO5 promoter, although the PHO2 binding site is right next to this motif (Vogel et al, 1989).

Figure 7B:
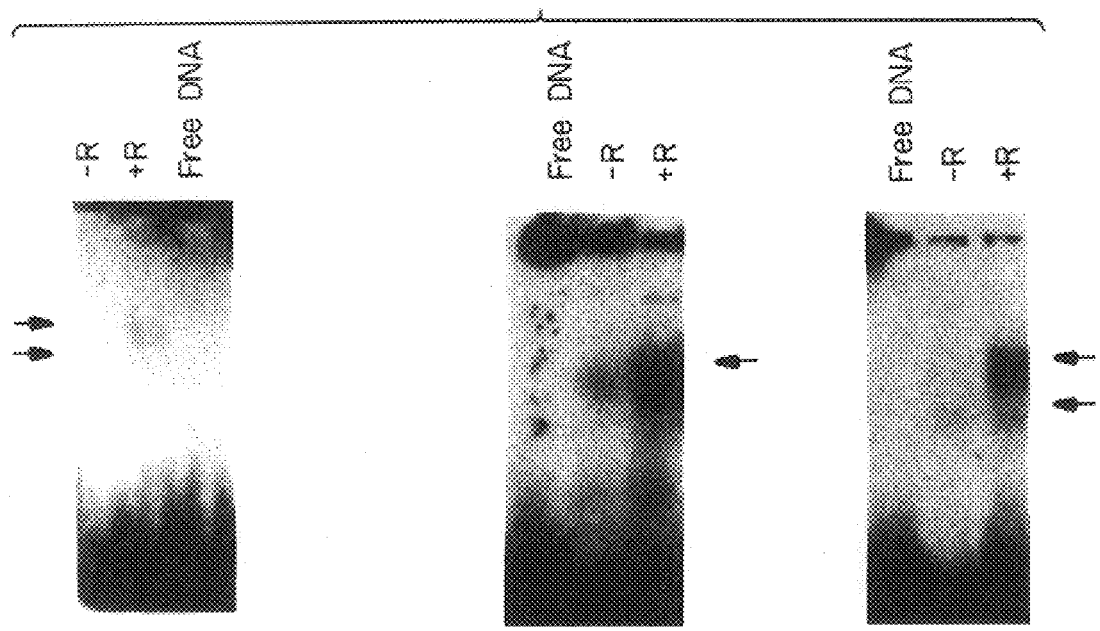

Synthetic double stranded oligonucleotides corresponding to each box were analyzed by EMSA in order to characterize DNA-protein interactions in the repeated segments (FIG. 7A). FIG. 7B illustrates that box I derived oligo DNA appears to form one type of complex of higher mobility with both root protein extracts and an additional lower mobility complex with the $P_i$-fed root proteins. As expected, the box II corresponding oligonucleotide forms a complex detectable with both protein extracts. In contrast, box III DNA incubation with different protein extracts resulted in formation of DNA-protein complexes with different electrophoretic mobilities. The slower migration of the DNA complexed with $P_i$-fed root proteins suggests binding of a larger trans-acting factor than the one present in the $P_i$-starved protein extract.

Figure 8:
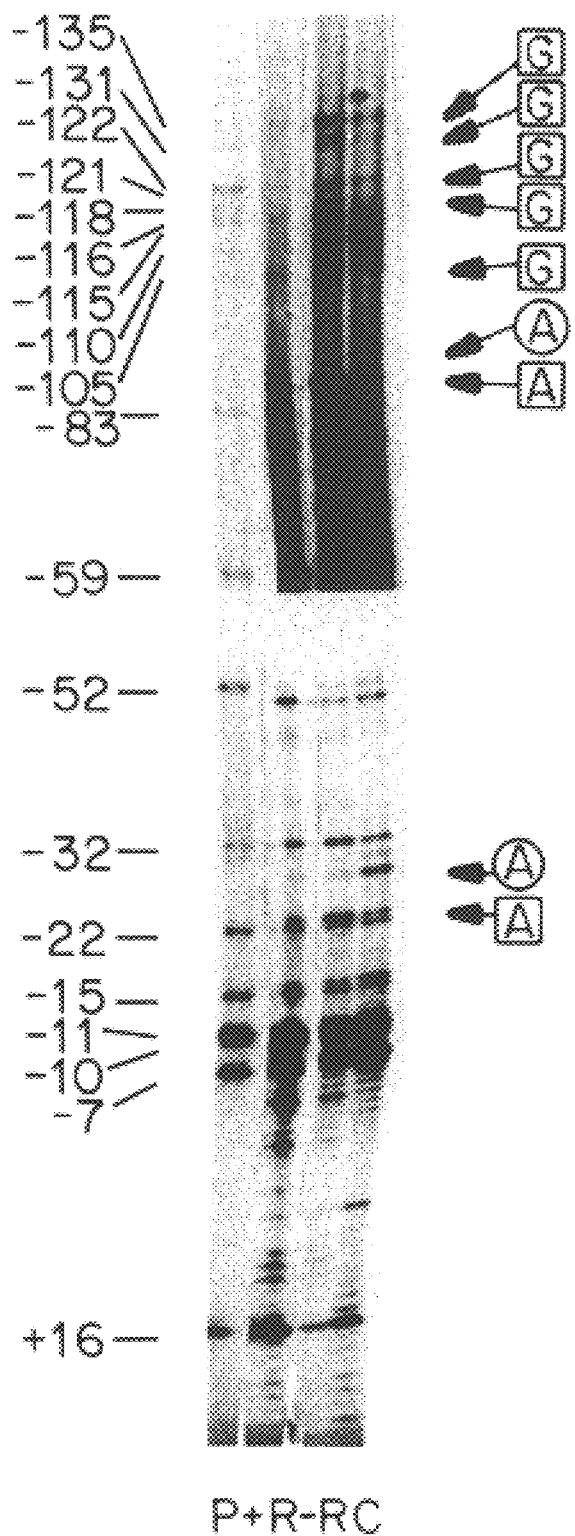
FIG. 8. Autoradiogram of in vivo DMS footprinting experiment. Protein contacts with the region proximal to the TATA box in the $P_i$-starved roots ($-R$) and the $P_i$-fed roots ($+R$) was displayed by comparing the in vivo DMS treatments of chromatin DNA with in vitro DMS treatment of purified genomic (C) or plasmid (P) DNA. Numbers on the left show the position of G residues in the top strand. The squared and circled residues on the right are the nucleotides with enhanced or reduced levels of DMS modifications, respectively, in $P_i$-starved and $P_i$-fed root tissues as revealed by ligation-mediated PCR (LM-PCR). Because of high intensities of the small DNA fragment bands, the bottom section of the gel was exposed to X-ray film for only one day (bottom) and the top section was exposed for several days (top).

A combination of dimethyl sulfate (DMS) footprinting and genomic DNA sequencing by LM-PCR methods were implemented to detect DNA-protein interactions in vivo (FIG. 8). In principal, DMS penetrates intact cells and modifies guanine and to a lesser extent adenine residues (Ferl and Nick, 1987) by the chemistry of Maxam and Gilbert sequencing reaction (Maxam and Gilbert, 1985; Dolan et al, 1995). However, where the proteins are in close associations with the DNA molecules, DMS modifications can be enhanced or suppressed, depending on the nature of the amino acid residues in contact with DNA (Ferl and Nick, 1987). After a brief exposure of cells to DMS, the partially methylated DNA is purified and cleaved at modified bases by piperidine. The resultant cleavage sites can then be visualized by either Southern blotting with a specific probe (Ferl, 1990) or by LM-PCR (Hammond-Kosak and Bevan, 1993).

The roots of *A. thaliana* seedlings treated with 5 mM $P_i$ or starved for $P_i$ for 14 days were exposed to 0.5% DMS for 10 min in order to obtain a reasonable number of random G modifications per DNA molecule. Purified DNA was digested with a restriction enzyme to reduce viscosity and cleaved with piperidine at modified residues. Following denaturation, an anti-sense primer close to the TATA box was used for primer extension. Sequencing Grade Taq DNA polymase was used in all DNA polymerization steps as it worked the best among all other tested enzymes. The cleavage sites were then revealed by 20 cycles of geometrical amplifications and another 10 cycles of arithmetical amplifications in which a radioactively-labelled primer with higher annealing temperature was employed. FIG. 8 shows the top and bottom portions of an autoradiogram illustrating the in vivo DMS footprints in $P_i$-starved and $P_i$-fed roots. Despite optimization procedures, there are still some extra bands (most corresponding to A residues) in addition to the expected bands that show cleavage at G residues. In comparison to the control lanes that are naked genomic or plasmid DNA exposed to DMS in vitro, enhancement of DMS alkylation can be detected for G residues positioned at −105, −118, −122, −131 and −135 (squared in FIGS. 2 and 8). Two of these, Gs at position −118 and −122, are located in the region that is bound by both $P_i$-fed and $P_i$-starved proteins (box II) and the other three Gs were only associated with proteins in $P_i$-starved roots (box I and box III). Several cases of variations in the intensity of extraneous bands were also observed (circled or squared in FIGS. 2 and 8). All of these bands coincided with the A residues in DNase I protected regions (FIG. 2).

As represented in FIG. 9, these results indicate the following:

1) The three repeated segments, particularly boxes I and III, are the most important regions in the $P_i$ concentration-dependent regulation of psr3.2 expression;
2) These segments are bound by several proteins present in $P_i$-fed and $P_i$-starved roots and a different set of proteins can bind under each condition;
3) The transcription initiation complex stably binds to the psr3.2 promoter only in the starved roots;
4) The transcription activators bound to box I could be essential for transmission of the activation signals coming from the upstream regions to the factors bound to DNA sequence between this box and the TATA box in the $P_i$-starved roots. In $P_i$-sufficient cells this function appears be blocked by a repressor that acts either by binding to the activator or by competing with it for the DNA binding site; It is possible there is more than one site for the activator because a long stretch of DNA is protected. The palindromic-like sequence is a candidate for the activator and the repressor binding sites. The position of this presumed repressor binding site is analogous to a −284 to −168 DNA sequence of a sugar-inducible plant promoter which rendered a negative effect on gene expression when fused between a reporter gene and a region for binding of positive factors (Sadka et al. 1994);
5) Box II is probably bound by the same factor under both $P_i$ treatments. This box could be a binding site for a general transcription factor with a function similar to the PHO2 protein of yeast as this region was protected by all proteins extracted from the roots and shoots (FIGS. 6A and C). PHO2, a general yeast trans-acting factor, binds between two other binding sites of PHO4 (Arndt et al, 1987). The PHO2 function in $P_i$ response has been postulated to assist PHO4 in nucleosome displacement (Fascher et al, 1990; Venter et al, 1994; Svaren et al, 1994);
6) Box III is bound by different trans-acting factors with each $P_i$ treatment; i.e., two or more activators and a repressor can bind in the starved and fed roots, respectively. Repetitive GTTCCA sequences suggest a cooperative binding of two or more regulatory proteins. The conserved CACAA motifs between psr3.2 could have a role in this regulatory process; and
7) The results of in vivo footprinting also support the respective regulatory regions being involved in the phosphate-starvation response of higher plants. The repeated DNA segment proximal to TATA box of psr3.2 promoter was investigated for in vivo DNA-protein interactions. In agreement with the in vitro results, five G residues were differentially represented in the autoradiogram indicating possible contacts with regulatory proteins (FIGS. 2 and 8), G residues positioned at −118 and −122 are located in box II which was shown to be protected from DNase I digestion by proteins present in extracts of both $P_i$-fed and -starved roots. The G residues at position −105 (box I), −131 and −135 (box III) were only protected by $P_i$-starved root proteins. In addition, lesser representations of several A residues within that region and within the TATA box are in agreement with the DNA-protein associations detected by in vitro experiments.

Nucleic Acids, Constructs and Vectors

One embodiment of this invention relates to a nucleic acid, such as SEQ ID NO:1 or portion thereof which comprises a regulatory region having at least one function characteristic of a phosphate-deficiency inducible promoter, such as directing expression of a phosphate-starvation response (psr) gene (e.g., psr3.2) and/or a different gene, in a plant or other photosynthetic organism. There is provided by this invention isolated DNA which, when operably linked to a structural gene, induces transcription of the structural gene in a cell derived from a photosynthetic organism under conditions of phosphate deficiency but not under conditions of phosphate sufficiency.

Further provided by this invention is isolated and/or recombinant DNA which comprises: (1) SEQ ID NO:1; (2) the ability to hybridize to; (a) a nucleic acid, such as a nucleic acid having the sequence of SEQ ID NO:1, or; (b) a portion of the foregoing which comprises a functional portion or fragment of SEQ ID NO: 1; or by (2) the ability to bind a transcriptional activation factor under conditions of $P_i$ deficiency or a repressor at a transcriptional activation binding site under conditions of $P_i$ sufficiency, or to comprise functional equivalents thereof; or (3) by both characteristics.

A nucleic acid which hybridizes to a nucleic acid capable of phosphate-deficiency inducible promoter activity such as SEQ ID NO:1, can be double- or single-stranded. Hybridization to DNA such as DNA having the sequence SEQ ID NO:1 includes hybridization to the strand shown or its complementary strand.

Those of skill in the art would recognize that not every nucleotide residue of a promoter sequence is essential for retention of promoter activity. The removal of or the substitution of a non-effective amount of nucleotide residues would not result in the loss of promoter activity; even the loss of 5–25% sequence similarity to the promoter region of SEQ ID NO:1 would not adversely affect promoter activity. In one embodiment, the percent nucleotide sequence similarity between a phosphate-deficiency inducible promoter such as SEQ ID NO:1 and functional equivalents thereof is at least about 50% ($\geq 50\%$). In a preferred embodiment, the percent nucleotide sequence similarity between a phosphate-deficiency inducible promoter and its functional equivalents is at least about 70% ($\geq$70%). More preferably, the percent nucleotide sequence similarity between a phosphate-deficiency inducible promoter and its functional equivalents is at least about 80%, and still more preferably, at least about 85%.

Isolated and/or recombinant nucleic acids meeting these criteria comprise nucleic acids having sequences identical to sequences of naturally-occurring (wildtype) regulatory nucleic acid sequences and portions thereof, or variants of the naturally-occuring genes. Such variants include mutants differing by the addition, deletion or substitution of one or more residues, modified nucleic acids in which one or more residues are modified (e.g., DNA or RNA analogs), and mutants comprising one or more modified residues.

Such nucleic acids, including DNA or RNA, can be detected and isolated by hybridization under high stringency conditions or moderate stringency conditions, for example, which are chosen so as to not permit the hybridization of nucleic acids having non-complementary sequences. "Stringency conditions" for hybridizations is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

High stringency hybridization procedures can (1) employ low ionic strength and high temperature for washing, such as 0.015 M NaCl/0.0015 M sodium citrate, pH 7.0 (0.1×SSC) with 0.1% sodium dodecyl sulfate (SDS) at 50° C.; (2) employ during hybridization 50% (vol/vol) formamide with 5× Denhardt's solution (0.1% weight/volume highly purified bovine serum albumin/0.1% wt/vol Ficoll/0.1% wt/vol polyvinylpyrrolidone), 50 mM sodium phosphate buffer at pH 6.5 and 5×SSC at 42° C.; or (3) employ hybridization with 50% formamide, 5×SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2× SSC and 0.1% SDS.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause, M. H. and S. A. Aaronson, *Methods in Enzymology,* 200:546–556 (1991). Also, see especially page 2.10.11 in *Current Protocols in Molecular Biology* (supra), which describes how to determine washing conditions for moderate or low stringency conditions. Washing is the step in which conditions are usually set so as to determine a minimum level of complementarity of the hybrids. Generally, from the lowest temperature at which only homologous hybridization occurs, a 1% mismatch between hybridizing nucleic acids results in a 1° C. decrease in the melting temperature $T_m$, for any chosen SSC concentration. Generally, doubling the concentration of SSC results in an increase in $T_m$ of ~17° C. Using these guidelines, the washing temperature can be determined empirically for moderate or low stringency, depending on the level of mismatch sought.

Isolated and/or recombinant nucleic acids that are characterized by their ability to hybridize to (a) a nucleic acid having phosphate-deficiency inducible promoter activity, such as the nucleic acid depicted as SEQ ID NO:1, (b) the complement of SEQ ID NO:1, (c) or a portion of (a) or (b) (e.g. under high or moderate stringency conditions), can further provide at least one function characteristic of a phosphate-deficiency deficiency inducible promoter activity, such as a transcription activation (e.g., induction of transcription of a gene of interest, such as psr3.2). The promoter function of a phosphate-deficiency inducible regulatory nucleic acid can be detected by standard enzymatic assays for activity or binding of the expressed protein or polypeptide (e.g., assays which monitor psr3.2 formation) encoded by the structural gene operably linked to the promoter. Functions characteristic of a psr3.2 protein or polypeptide may also be assessed by in vivo complementation activity or other suitable methods. Enzymatic assays, complementation tests, or other suitable methods can also be used in procedures for the identification and/or isolation of nucleic acids which encode a polypeptide such as a psr polypeptide, or a functional equivalent of this polypeptide. The antigenic properties of proteins or polypeptides encoded by structural genes linked to hybridizing nucleic acids can be determined by immunological methods employing antibodies that bind to a psr polypeptide, such as immunoblot, immunoprecipitation and radioimmunoassay.

Nucleic acids of the present invention can be used in the production of peptides, polypeptides or proteins. For example, DNA containing all or part of the functional sequence for a phosphate-deficiency inducible promoter, or DNA which hybridizes to DNA having the sequence SEQ ID NO:1, can be incorporated into various constructs and vectors created for further manipulation of structural nucleic acid sequences or for production of the encoded peptide, polypeptide or protein in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow or make probable a desired recombination event.

A further embodiment of the invention is antisense nucleic acid operably linked to a promoter of this invention, which is complementary, in whole or in part, to a target molecule comprising a sense strand, and can hybridize with the target molecule. The target can be DNA. When introduced into a cell, antisense nucleic acid can inhibit the activity of the gene represented by the sense strand. Antisense nucleic acids can be produced by standard techniques.

In a particular embodiment, the antisense nucleic acid is wholly or partially complementary to and can hybridize with a target nucleic acid, wherein the target nucleic acid can hybridize to a nucleic acid, or a portion thereof, having the sequence of the complement of the DNA strand whose transcription is initiated by the regulatory region in SEQ ID NO:1 and FIGS. 2A–2B. For example, antisense nucleic acid can be complementary to an endogenous structural gene encoding the sequence of a psr protein or to a portion thereof sufficient to allow hybridization and effectively inhibit the expression and activity of the protein under $P_i$ deficient conditions. Antisense nucleic acids can be produced by standard techniques. See, for example, Shewmaker, et al., U.S. Pat. No. 5,107,065.

In addition to the antisense nucleic acids of the invention, oligonucleotides can be constructed which will bind to duplex nucleic acid either of the phosphate-deficiency inducible regulatory region to form a stable triple helix-containing or triplex nucleic acid to inhibit promoter activity and consequently the transcription and/or expression of a linked structural gene. Frank-Kamenetskii, M. D. and Mirkin, S. M. (1995) *Ann. Rev. Biochem.* 64:65–95. Such oligonucleotides of the invention are constructed using the base-pairing rules of triple helix formation and the nucleotide sequence of the phosphate-deficiency inducible regulatory region. These oligonucleotides can block promoter activity in a number of ways, including prevention of binding of transcription activators or by binding to repressor binding sites and thus mimicking the activity of a repressor.

The DNA provided by this invention can also be used to isolate homologous nucleic acids from the same and other species of plants or photosynthetic organisms which encode genes involved in the phosphate deficiency response. In this context, homology means an overall sequence identity of at least 50%, preferably 70% or more for the trans-activation/repressor portion of the promoter identified in SEQ ID NO:1. The identification and isolation of phosphate-deficient promoter sequences of other photosynthetic organisms is carried out according to standard methods and procedures known to those of ordinary skill in the art. See, e.g., Sambrook, et al. (1989) *Molecular Cloning—A Laboratory Manual*, Cold Spring Harbor Laboratory Press, Cold Spring Harbor, N.Y. An example of this application is found in Example 5, infra.

By using these and other similar techniques, those of ordinary skill can readily isolate not only the regulatory region of different plant species, but also homologues of these nucleic acids from other photosynthetic organisms. By example, phosphate-deficient promoters in plants can be identified by preparing a genomic or cDNA library of a plant species; probing the genomic or cDNA library with all or a portion or a homologue of SEQ ID NO:1; identifying the hybridized sequences; and isolating the hybridized DNA to obtain the phosphate-deficient promoter of that plant. Once identified, these genes can be restriction mapped, sequenced and cloned. In particular, the Box I-III regions or fragments thereof are especially effective as probes because of their conserved homology to other species' regulatory regions. Fragments as small as 20 bp in length, preferably 50 or 100 bp in length, can be used to hybridize to other conserved regulatory regions.

The isolated gene is representative of a broader class of genes derived from various species of photosynthetic organisms. These additional genes can also be used to induce expression of numerous genes, with utilities corresponding to those described herein, and can be used in the production of host cells and photosynthetic organisms comprising recombinant phosphate-deficiency inducible promoters using methods described herein. The approaches described herein, including, but not limited to, the approaches to isolate and manipulate a phosphate-deficiency inducible promoter to construct vectors and host strains, and to produce and use the expressed proteins, to produce insecticides, antibodies, etc., can be applied to other photosynthetic organisms as described herein.

For example, a nucleic acid comprising a phosphate-deficiency regulatory region can be produced by methods such as PCR amplification. For instance, to isolate a phosphate-deficiency regulatory region of another photosynthetic organism, or portion thereof, primers specific to portions of the phosphate-deficiency inducible promoter (SEQ ID NO:1, FIGS. 2A–2B), such as the residues shown in boxes I, III or III of FIG. 7A can be used together or in combination with other suitable primers, or primers designed based upon the *A. thaliana* promoter sequence) in a PCR amplification reaction using a suitable template (e.g., genomic DNA, a library containing DNA from a species of a plant).

Consideration of this information, along with the remaining teachings of the specification, allows the construction of phosphate-deficiency inducible regulatory regions which possess at least one function characteristic of a psr3 promoter; that is, the capability of binding repressors during periods of phosphate sufficiency or activators during periods of phosphate deficiency.

Methods of Producing Recombinant Nucleic Acids, Vectors and Transgenic Organisms This invention further relates to a method of producing a phosphate-deficiency inducible regulatory region, such as SEQ ID NO:1, or a portion thereof, linked to a gene of interest, and to expression systems and host cells containing a vector appropriate for expression of a gene of interest.

Cells that express a recombinant phosphate-deficiency inducible regulatory region or a portion thereof, linked to a gene of interest, can be made and maintained in culture under conditions suitable for expression to produce protein for isolation and purification. These host cells can be prokaryotic or eukaryotic. Preferred eukaryotic cells are plant cells derived from agronomically or horticulturally-important species. These include monocot, dicot, and gymnosperm species, as well as the nonvascular plants. Other photosynthetic organisms, such as the multicellular and unicellular algae can also be modified. Examples of prokaryotic cells that can be used to express structural genes under control of the regulatory regions of this invention include the cyanobacteria, such as *Anacystis nidulans* or Spirulina sp. In one embodiment, host cells that produce a recombinant phosphate-deficiency inducible promoter or portion thereof for isolation and purification, can be made as follows. DNA comprising a phosphate-deficiency inducible promoter or functional portion thereof can be inserted into a nucleic acid vector, e.g., a DNA vector, such as a plasmid, virus or other suitable replicon, which can be present in a single copy or multiple copies, or the DNA can be integrated in a host cell chromosome. The vector can be any vector which expresses the exogenous DNA in cells of photosynthetic organisms into which the vectors are introduced.

Suitable plant transformation vectors include those derived from a Ti plasmid of *Agrobacterium tumefaciens*, as well as those disclosed, e.g., by Herrera-Estrella, et al. (1983) *Nature* 303:209; Klee, H. J., et al. (1985) *Bio/Technology* 3:637–42; and EPO publication 120,516 (Schilperoort, et al.). In addition to plant transformation vectors derived from the Ti or root-inducing (Ri) plasmids of Agrobacterium, alternative methods can be used to insert the nucleic acid construct of this invention into cells of photosynthetic organisms. Such methods can involve, e.g., the use of liposomes, electroporation, chemicals that increase free nucleic acid uptake, free DNA delivery via microprojectile bombardment, abrasion of plant cells in the presence of DNA, and transformation using viruses or pollen. A suitable replicon can contain all or part of the DNA sequence for a phosphate-deficiency inducible promoter operably linked to one or more structural genes of interest whereby the structural sequence is under the control of the phosphate-deficiency inducible promoter and linked to appropriate translation signals to permit translation of the encoded RNA thereof.

In addition to 5' leader sequences, terminator sequences are usually incorporated into the construct. In plant constructs, a 3' untranslated region (3'UTR) is generally part of the expression plasmid and contains a polyA termination sequence. The termination region which is employed will generally be one of convenience, since termination regions appear to be relatively interchangeable. The promoter can be truncated or the activator and/or receptor sites modified. Other modifications, such as base changes to optimize codon usage or addition of one or more enhancer sequences can further improve expression of the structural gene. Alternatively, the distance between the promoter and the structural gene can be lengthened by the addition of bases upstream from the ATG start site to vary the degree of expression of the structural gene.

The vector can be introduced into cells by a method appropriate to the type of host cells (e.g., transformation, electroporation, transfection). For the purposes of this disclosure, the terms "transformed with", "transformant", "transformation", "transfect with", and "transfection" all refer to the introduction of a nucleic acid into a cell by one of the numerous methods known to persons skilled in the art. Transformation of prokaryotic cells, for example, is commonly achieved by treating the cells with calcium chloride so as to render them "competent" to take up exogenous DNA, and then mixing such DNA with the competent cells. Prokaryotic cells can also be infected with a recombinant bacteriophage vector.

Nucleic acids can be introduced into cells of higher organisms by viral infection, bacteria-mediated transfer (e.g., Agrobacterium T-DNA delivery system), electroporation, calcium phosphate co-precipitation, microinjection, lipofection, bombardment with nucleic-acid coated particles or other techniques, depending on the particular cell type. For grasses such as corn and sorghum, microprojectile bombardment as described, for example, in Sanford, J. C., et al., U.S. Pat. No. 5,100,792 (1992) can be used. Other useful protocols for the transformation of plant cells are provided in Gelvin et al., 1992. Suitable protocols for transforming and transfecting cells are also found in Sambrook et al., 1989. The nucleic acid constructs of this invention can also be incorporated into specific plant parts such as those described supra through the transformation and transfection techniques described herein.

To aid in identification of transformed plant cells, the constructs of this invention are further manipulated to include genes coding for plant selectable markers. Useful selectable markers include enzymes which provide for resistance to an antibiotic such as gentamycin, hygromycin, kanamycin, or the like. Similarly, enzymes providing for production of a compound identifiable by color change such as GUS (β-glucuronidase), or by luminescence, such as lucifase, are useful.

For example, active β-glucosidase can be produced by integrating a psr3.2 gene encoding *A. thaliana* phosphate-starvation induced β-glucosidase which is linked to the DNA comprising SEQ ID NO:1 into the genome of a virus that enters the host cells. By infection of the host cells, the components of a system which permits the transcription and translation of the β-glucosidase gene are present in the host cells. For expression of the structural gene, the host cells can be maintained under appropriate conditions, e.g., phosphate-limited growth conditions, etc.

When cells or protoplasts containing the gene of choice driven by a promoter of the present invention are obtained, the cells or protoplasts are regenerated into whole plants. The transformed cells are then cultivated under conditions appropriate for the regeneration of plants, resulting in production of transgenic plants. Choice of methodology for the regeneration step is not critical, with suitable protocols being available for many varieties of plants, tissues and other photosynthetic organisms. See, e.g., Gelvin S. B. and Schilperoort R. A., eds. *Plant Molecular Biology Manual, Second Edition,* Suppl. 1 (1995) Kluwer Academic Publishers, Boston Mass., U.S.A.

Transgenic plants carrying the construct are examined for the desired phenotype using a variety of methods including but not limited to an appropriate phenotypic marker, such as antibiotic resistance or herbicide resistance as described supra, or visual observation of the growth under varying levels of phosphate compared to the growth of the naturally-occurring plants under the same conditions.

As used herein, the term transgenic plants includes plants that contain either DNA or RNA which does not naturally occur in the wild type (native) plant or known variants, or additional or inverted copies of the naturally-occurring DNA and which is introduced as described herein. Transgenic plants include those into which isolated nucleic acids have been introduced and their descendants, produced from seed, vegetative propagation, cell, tissue or protoplast culture, or the like wherein such alteration is maintained. Such transgenic plants include, in one embodiment, transgenic plants which are angiosperms, both monocotyledons and dicotyledons. Transgenic plants include those into which DNA has been introduced and their progeny, produced from seed, vegetative propagation, cell, tissue or protoplast culture, or the like.

Seed can be obtained from the regenerated plant or from a cross between the regenerated plant and a suitable plant of the same species. Alternatively, the plant can be vegetatively propagated by culturing plant parts under conditions suitable for the regeneration of such plant parts.

In yet another aspect of this invention are provided plant tissue culture and protoplasts which contain DNA comprising an altered or exogenously introduced phosphate-deficiency inducible promoter operably linked to a structural gene, which alters the response of the tissue culture or protoplasts to varying levels of phosphate in the environment.

The methods of this invention can be used with in planta or seed transformation techniques which do not require culture or regeneration. Examples of these techniques are described in Bechtold, N., et al. (1993) *CR Acad. Sci. Paris/Life Sciences* 316:1 118–93; Chang, S. S., et al. (1990) *Abstracts of the Fourth International Conference on Arabidopsis Research*, Vienna, p. 28; Feldmann, K. A. and Marks, D. M (1987) *Mol. Gen. Genet.* 208:1–9; Ledoux, L., et al. (1985) *Arabidopsis Inf Serv.* 22:1–11; Feldmann, K. A. (1992) In: Methods in Arabidopsis Research (Eds. Koncz, C., Chua, N-H, Schell, J.) pp. 274–289; Chee, et al., U.S. Pat. Ser. No. 5,376,543.

Applications

Phosphate-starvation responses are very important to photosynthetic organisms. Because advances in the understanding and function of promoters which induce phosphate-starvation inducible responses would be of tremendous benefit in agriculture, promoters which can induce these responses are extremely important in transgenic biology.

This invention makes possible transgenic plants in which phosphate uptake or regulation thereof is altered by the promoter during the synthesis of phosphate transporters. Transgenic plants are provided in which the phosphate uptake is greater than it is in the corresponding naturally-occurring or wild type (native) plant. Alternatively, plants can be produced in which phosphate uptake is reduced at particular stages in the lifespan of the plant or in particular cells and tissues.

The phosphate-deficiency inducible promoter or a homologue thereof can be altered and introduced into a plant to alter the phosphate uptake of the plant so that it can be grown in a different soil from the one in which the parent strain is adapted. For example, the repressor-binding sites can be altered so repressor proteins no longer bind to the promoter and the promoter acts in a constitutive manner. Thus, an engineered phosphate-deficiency inducible promoter can be incorporated into a plant variety which has been bred for other traits (e.g., high yield and disease resistance), to produce a plant variety that can glean additional phosphate from its environment.

Transgenic plants of this invention can contain isolated or recombinant nucleic acids which preferentially modify phosphate transport pathways which are present in tissues of all parts of the plant, or which are present in actively growing tissues or in storage tissues or organs such as seeds. The phosphate-regulated pathways of plant tissues are desirable targets for modifications to provide increased photosynthetic capacity or to provide mechanisms for disease or stress resistance. Alternatively, transgenic plants can contain introduced isolated or recombinant nucleic acids which alter the transport capability metabolism of the roots, shoots and leaves of plants. In this manner, different products can be accumulated, exported or imported to modify the capability of the plant to express and localize one or more products compared to the expression and accumulation of the same product(s) in a plant of the same variety without said introduced isolated or recombinant nucleic acids when grown under identical conditions.

Further, this invention includes a method of producing a transgenic plant containing isolated nucleic acids which comprise a phosphate-deficient inducible promoter or its functional equivalent which initiates the transcription of at least one nucleic acid which encodes a polypeptide for production of a useful product. Coupled with the altered membrane transport system in the cells of the plant, it is possible to design a plant wherein, when all of the inserted nucleic acids are expressed, the result is the large scale and inexpensive production of valuable proteins or other products in a particular plant tissue or at a particular level of available phosphate.

These plants can be grown in conventional hydroponic culture media to provide an efficient system by which the plants can be deprived of phosphate to induce protein synthesis. Further, using a hydroponic culture system permits quick and efficient harvesting of roots and other plant parts for isolation of products.

Further, the promoter of this invention can induce expression of an encoded protein which functions as a limiting enzyme in a metabolic pathway, thus providing a regulatory function for the plant. The ability to regulate the pathway by varying $P_i$ levels would allow, for example, production of a product when the plant reached a particular point in growth. The product could be a harvestable compound or it could have a regulatory function, such as flower evocation.

The promoter of this invention is useful to induce root abundant expression of a structural gene to which it is operably linked. However, this promoter or portions thereof can also exhibit shoot activity and can induce expression of a structural gene of interest in other parts of multicellular photosynthetic organisms.

The promoter provided by this invention can be used to drive the expression of genes, either endogenous or foreign, to protect plants from diseases and pests to which the plant is most susceptible under conditions of low available phosphate (less than 1 mM exogenous $P_i$). For example, in addition to endogenous promoters which, under phosphate-deficient conditions, initiate additional phosphate uptake through secretion of acids and phosphatases, an additional construct wherein a phosphate-deficiency inducible promoter induces expression of Bt insecticidal toxins could be an advantage to a crop or horticultural species. Or, an additional construct can be inserted in which the promoter is linked to a gene encoding a chitinase to produce high localized levels of chitinases to prevent or resist fungal attack.

The promoter of this invention can be particularly useful for controlling nematode attack. Nematodes are primitive eukaryotic root parasites. These small worms live in the soil where they puncture plant roots and suck the cellular contents, weakening the plant and providing an entry point for pathogenic fungi and bacteria. β-glucosidase (such as psr3.2) expression is increased when nematodes attack roots, suggesting that changes in $P_i$ regulation are part of the plant's resistance mechanism to nematode injury. This indicates that the promoter of this invention is responsive to nematode invasion as well as $P_i$ limitation, which makes it useful for applications to control nematode injury.

For example, the promoter of this invention can be linked to a gene encoding a nematode toxin, so that, under nematode attack, the toxin is expressed locally when and where it is required. This mechanism would be an efficient and cost-effective improvement in nematode control which presently consists of applying pesticides to the soil for two to three weeks.

The promoter of this invention can be used to control expression of a great variety of compounds. For example, expression of extra storage protein, pigments, oils can be triggered at the time of flowering, seed development, and the like. Alternatively, the promoter can be used to drive genes which alter the ripening characteristics of fruit, including but not limited to, proteins affecting the levels of color, flavor and speed of development. Those of skill in the art will recognize the advantages of these promoters fused to genes of interest in particular species of plants and other photosynthetic organisms.

Another application of this technology to plants is to decrease the vegetative phase (and therefore shorten the time to flowering) of crops that are harvested for flowers, fruits and seeds. Additional copies of a phosphate-deficiency inducible promoter linked to a regulatory gene whose expression results in uptake of additional phosphate from the environment could increase the phosphate to nitrogen ratio in the plant. This, in turn, can cause floral induction and earlier flowering.

For plants harvested for their vegetative parts such as stems and leaves (e.g., lettuce, cabbage, spinach, maize) antisense sequences to an endogenous regulatory or structural gene as described above could be linked to introduced copies of a phosphate-deficient inducible promoter. Under limiting phosphate conditions, expression of the antisense gene could inhibit transcription or translation of the endogenous regulatory gene, thereby preventing increased uptake of phosphate and increasing the ratio of nitrogen to phosphorus in the plant. The result would be to increase yield of these crops by delaying flowering. Alternatively, with knowledge of the activation sites of the endogenous promoter, as described herein, proteins could be developed which block the activation sites, preventing expression of the regulatory or other protein.

Thus, any plant may be employed in accordance with this invention, including angiosperms, gymnosperms, monocotyledons, and dicotyledons. Plants of interest include cereals such as wheat, barley, maize, sorghum, triticale, etc.; other commercially-valuable crops, such as sunflower, soybeans, safflower, canola, etc.; fruits, such as apricots, oranges, apples, avocados, etc; vegetables, such as carrots, lettuce, tomatoes, broccoli, etc; woody species, such as poplar, pine, oak, etc; and ornamental flowers, such as clematis, roses, chrysanthemums, tulips, etc.

Plant cell cultures are a potential source of products. In addition to endogenous plant products, transgenic plant cells or tissue culture can be a valuable source of bacterial, fungal and animal compounds. Medicines, dyes, enzymes, flavoring agents, aromatic oils, hormones, immune system components, and the like can be produced in plant cells. Commercially important plant products which are synthesized only in small quantities or at particular growth or flowering stages, or which are unique to plants not amenable to agriculture.

It is difficult to profitably produce products by plant cell or tissue culture, however, because such culture results in insufficient production and secretion of the target product, poor cell growth, and difficulties in maintaining the appropriate cell type in culture. Cells or tissue culture incorporating additional exogenous phosphate-deficiency inducible promoters linked to genes encoding psr proteins, however, could increase phosphate uptake and provide more efficient growth, thus improving production while reducing the costs of supplying a major nutrient.

The phosphate-triggered regulatory sequence provided by this invention can be used to control and enhance production of commercial compounds synthesized when transcription of a gene or several genes is turned on through linking of the gene to the regulatory sequence. The supply of phosphate to the cells or tissue can be used to control this production at particular times. Thus, in tissue culture of tissues derived from plants and other photosynthetic organisms, the promoter can drive a gene for a specific product and the product levels can then be increased on demand by lowering the level of phosphate in the culture medium.

The regulatory sequence provided by this invention can also be used to detect transformation in plant cells or the cells of photosynthetic organisms. Thus, a method of detecting transformation in a cell of a group of cells, a tissue or an organism can comprise: incorporating a DNA comprising a phosphate-deficiency inducible promoter and another gene (under control of promoter) encoding a product into the cell; and maintaining the cell under phosphate-deficient conditions appropriate for promoter activity so that the product is expressed so that wherein expression of the product is indicative of a transformed cell.

The L5 plasmid containing clone L5 in pBluescript II KS+/-(Stratagene, La Jolla, Calif., U.S.A.) was deposited on, Feb. 25, 1997, with the American Type Culture Collection (ATCC), 12301 Parklawn Drive, Rockville, Md. 20852 and is available under the accession No. 97894.

All citations in this application to materials and methods are hereby incorporated by reference.

The following examples describe specific aspects of the invention to illustrate the invention and provide a description of the methods used to isolate and characterize a phosphate-deficiency inducible promoter and to identify its function in photosynthetic organisms. The examples should not be construed as limiting the invention in any way.

EXEMPLIFICATION

Example 1

Cloning of psr3 Promoter Region

The EcoRi–SalI fragment of Arabidopsis genomic clone 40F (clone L5) obtained by using *Brassica nigra* psr3.1 cDNA as a probe (Malboobi and Lefebvre, 1996a) was subcloned into Bluescript II KS+/-phagemid (Stratagene, La Jolla, Calif.) and introduced into *E. coli* strain DH5-α by standard procedures (Sambrook et al., 1989).

Example 2

Nuclear Run-Off Analysis

Plasmid DNA carrying the *Brassica nigra* psr 3.1 cDNA or *Arabidopsis thalilana* α-tubulin inserts was alkaline denatured and applied to Nytran-Plus (Schleicher and Schuell, Keene, N.H., U.S.A.) at a concentration of five μg DNA per dot using Bio-Dot Microfiltration apparatus (Bio-Rad, Hercules, Calif., U.S.A.). To produce probes from newly synthesizing mRNA species, transcriptionally-active nuclei were isolated from 5–6 g of 5 mM $P_i$-fed and $P_i$-starved root tissues by methods described in Willimizer and Wanger (1981). Transcription was allowed to proceed in the presence of $^{32}$P-UTP for 60 min at 30° C. using the method of Chappel and Hahlbrock (1984). The labelled RNA was purified as described by Somssich et al. (1989). Approximately $10^6$ cpm of RNA probes was used for hybridization with the dot blots as described in Malboobi and Lefebvre (1995). After the last wash, the blot was treated with 20 μg/ml of ribonuclease A in 2X SSC for 30 min at room temperature. The blot was then washed twice with 2×SSC, 0.5% SDS and twice with 2×SSC. The dot blots were then exposed to X-ray film for 7 or more days.

Transcription was allowed to proceed in the presence of $^{32}$P-UTP in the isolated nuclei from $P_i$-starved ($-P_i$) and $P_i$-fed ($+P_i$) roots. The labelled RNA were then hybridized with psr3 and -tubulin DNA dotted onto a nylon membrane. There is higher intensity of signal for the psr3 nuclear run-off products of $P_i$-starved nuclei than for those of $P_i$-fed nuclei as compared to the signals for the c-tubulin mRNA synthesis as an internal control.

Example 3

Preparation of Crude Nuclear and Whole Cell Protein Extracts

Small scale preparations of nuclear protein extraction were performed by a modification of the method of Dercker and Gannon (1994). About 500 mg of 14-day-old, $P_i$-starved or $P_i$-fed roots A. thaliana (Malboobi, M. A. and Lefebrve, D. D. (195)) were ground to fine powder by a mortar and pestle in liquid nitrogen. The powder was added to and thawed in 5 ml of Buffer A containing 0.25 M sucrose, 10 mM NaCl, 10 mM MES, pH 6.0, 5 mM EDTA, 0.15 mM spermidine-HCl (Sigma, St. Louis, Mo., U.S.A.), 0.6% nonidet P-40 (Sigma), 1% bovine serum albumin (Sigma), 20 mM beta-mercaptoethanol (Sigma) and 0.2 M phenylm-ethylsulfonyl fluoride (PMSF; Sigma). All steps from this point were done on ice. To increase the yield of isolated nuclei, the tissue was further homogenized with a Dounce homogenizer (7 strokes) and filtered successively through 130, 80 and 20 μm nylon mesh. The remaining debris was removed by a brief centrifugation (300×g) and the supernatant transferred to fresh 15 ml tubes and centrifuged at 2000×g for 1 min to pellet the nuclei. Nuclei were resuspended in 100–200 μl of buffer B (20 mM Tris-HCl pH 7.2, 420 mM NaCl, 1.2 mM $MgCl_2$, 0.2 mM EDTA, 0.5 mM dithiothreitol (DTT; Sigma), 25% glycerol, 0.5 mM PMSF, 5 μg/ml antipain (Sigma), 5 μg/ml leupeptin (Sigma)), then placed on ice for 30 min for high salt extraction. The lysed nuclear debris was pelleted in a desktop microfuge and the supernatant collected. Protein concentration of the supernatant was determined spectrophotometrically by using the Bio-Rad protein assay reagents according to the manufacturer (Bio-Rad Laboratories, Hercules, Calif., U.S.A.). Small aliquots of each extract were frozen in liquid nitrogen and stored at −80° C. Whole cell protein extracts were prepared on a large scale by ammonium sulfate precipitation method according to Foster and coworkers (1992).

Example 4

Electrophoresis Mobility Shift Assays

The restriction enzyme products (BamHI-HpaI, HpaI-BglII, HpaI-EcoRV, and EcoRV-DraI DNA fragments) and double stranded synthetic oligonucleotides were $^{32}$P-labelled either with the Klenow fragment of DNA polymase I (Pharmacia, Baie D'Urfe, Quebec, Canada) or $T_4$ polynucleotide kinase (Promega, Madison, Wis.) using standard methods according to Sambrook et al. (1989). Probes were purified from the labelling reaction either by passing through ProbeQuant™ micro columns (Pharmacia) or by cutting the agarose gel bands, followed by DNA isolation using an Elu-Quik DNA purification kit (Schleichler & Schuell, Keene, N.H.). The optimized reaction was composed of 40,000 or more cpm of probe, 25 μg of protein extracts, 0.5 μg of sheared herring sperm DNA (Promega) in binding buffer (7.5 mM Tris-HCl pH 7.2, 42 mM NaCl, 1 mM EDTA, 10% glycerol, 2.5 mM $CaCl_2$, 0.5 mM spermidine and 0.2 mM PMSF) in a final volume of 10 μl. Herring DNA was added to protein extracts prior to or with the probes. The mixture was incubated at room temperature for 20–30 min before loading on a non-denaturing 4–5% polyacrylamide gel buffered with 0.5×TBE (45 mM Tris-borate, 1 mM EDTA). The gel was cast in a Bio-Rad mini-gel system and pre-run in 0.5×TBE tank buffer for 60 min at 60 V. After loading the DNA-protein mixtures, the gel was run for 30 min at 150 V at room temperature. Gels were sandwiched between two pieces of gel drying films (Promega) overnight and exposed to X-ray films as described above.

Example 5

In Vitro Footprinting With DNASE I

Figure 5:
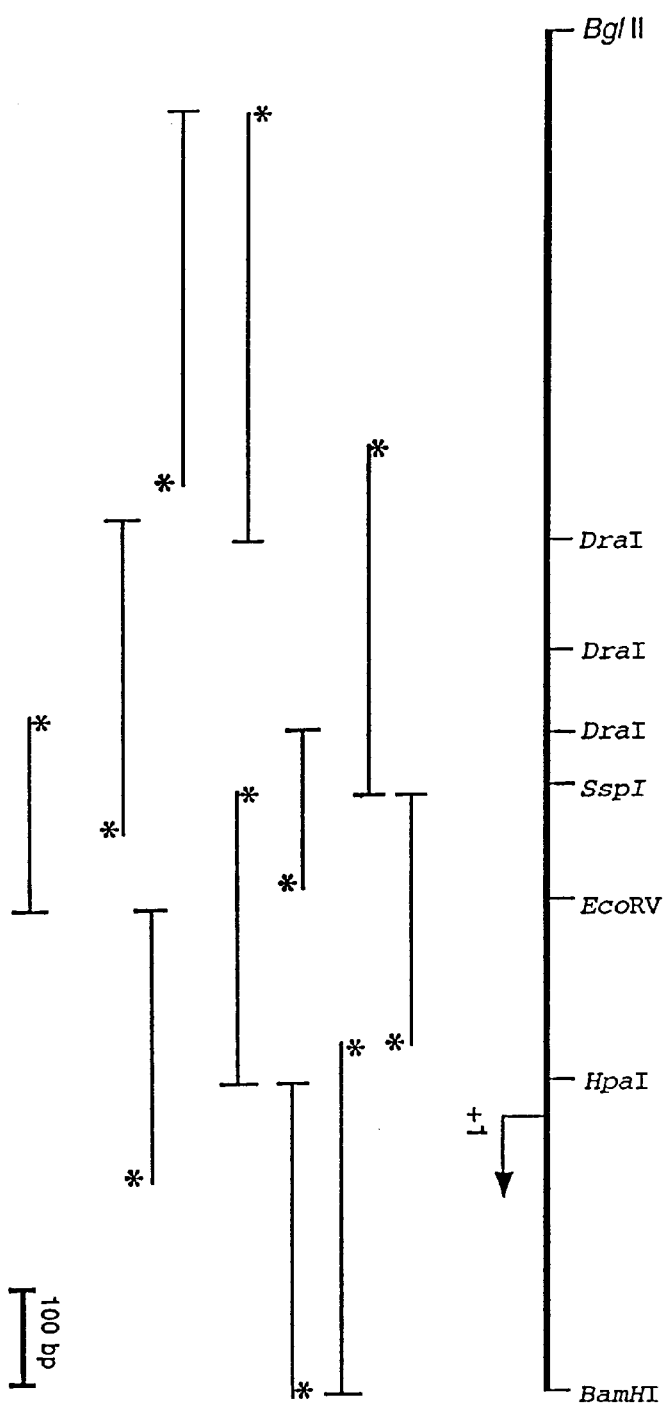
FIG. 5. DNA fragments used for DNase I footprinting. The fragments were produced by PCR amplification followed by purification of the corresponding band from agarose gel. Each fragment was labelled by using $[\gamma^{32}P]$-dATP and $T_4$ polynucleotide kinase. The fragments were then cut by restriction enzymes to produce unidirectionally labelled probes. After running the second agarose gel and DNA purification, probes were incubated with protein extracts and treated with DNase I. The labelled ends and restriction enzyme sites are indicated by asterisks (*) and vertical lines, respectively.
Figures 6A, 6B:
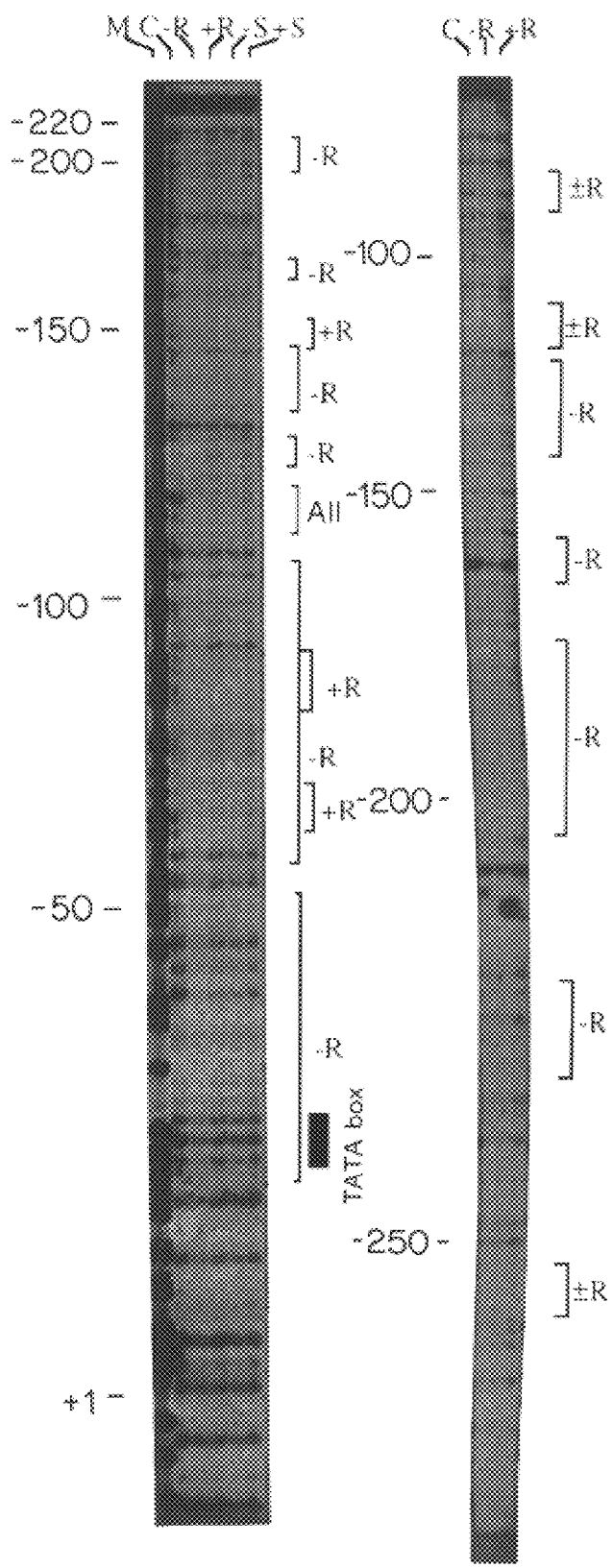

The DNA fragments for the regions indicated in FIG. 5 were amplified by PCR using Taq Plus Polymase (Biotechnology Department, Sangon Ltd., Scarborough, Ontario, Canada). The DNA bands were purified from agarose gels and at their 5'-ends with $T_4$ polynucleotide kinase as above. Unidirectionally-labelled DNA fragments were created by digestion with the restriction enzymes as indicated in FIG. 5. More than 100,000 cpm of each probe was incubated with 50 μg of whole cell protein extract and 1 μg of sheared herring sperm DNA in a final volume of 25 μl of binding reaction with salt concentrations as described for electrophoresis mobility shift assays. DNase I treatment was conducted after 20–30 min incubation at room temperature. Two μl of 15 mg/ml DNase I and 0.375 mM $MgCl_2$ was added, mixed quickly and incubated for exactly 60 sec at room temperature prior to adding 100 μl of stop solution (0.1 mM EDTA, 0.6 M $NH_4COOH$, 20 μg/ ml herring sperm DNA). The DNA was retrieved by phenol:chloroform extraction and ethanol precipitation. The DNA pellets were dissolved in 6 μl of sequencing dye (80% deionized formamide, 0.5×TBE, 0.08% bromphenol blue and 0.08% xylene-cyanol) and loaded on to a 7% polyacrylamide sequencing gel.

Example 6

In Vivo Footprinting with Dimethyl Sulfate

A. thaliana seedlings were starved for $P_i$ or fed with 5 mM Pi for 14 days. Root and shoot tissues were separated and soaked immediately in 50 ml half strength minus $P_i$-MS medium containing 0.5% dimethyl sulfate (DMS; Acros Organic, New Jersey, N.J.). The solution was infiltrated into the intracellular spaces by applying vacuum and then releasing it slowly for a total duration of 10 min. The tissues were washed three times with 500 ml of cold half-strength MS medium and frozen in liquid nitrogen. DNA was extracted from DMS-treated and normal plant tissues, and digested with EcoRI enzyme. As controls, DNA from untreated plants and also the L5 plasmid DNA containing the psr3.2 promoter sequence were exposed to 1% DMS in 10 mM $MgCl_2$, 50 mM sodium cacodylate (Fisher Scientific, Fair Lawn, N.J.) (pH 8.0), and 1 mM EDTA for 2 min at room temperature. All DNA samples were extracted once with phenol: chloroform and once with chloroform prior to precipitation with ethanol. The DNA pellet was dissolved in 100 μl of 1:10 piperidine (Fisher Scientific), diluted in water and incubated for 30 min at 90° C. DNA was then precipitated in 0.3 M sodium acetate and ethanol. $P_i$ peridine was removed vigorously by drying the DNA pellet under vacuum for several hrs, redissolving in water and freeze-drying in a Speed-Vac overnight.

About 10 µg of genomic DNA or 1 ng of plasmid DNA were added to the ligation-mediated PCR (LM-PCR) reactions in which Sequencing Grade Taq DNA polymase enzyme (Promega) was used in all three steps. Using 2 pmole of primer L5T72 (AGCAAAAGCAGCCCCATGAGAGGAA), the primer extension reaction was done in 50 µl of 100 µM dNTPs, 4 mM MgSO$_4$, 10 mM Tris-HCl (pH 9.0), 5 mM KCl, 0.1% Triton X-100 and the above template DNA. Samples were heated at 94° C. for 10 min, 2.5 units of the enzyme were added and then incubated at 55° C. for 20 min and 70° C. for 10 min for two cycles. After phenol: chloroform extraction and ethanol precipitation, the DNA was ligated to 100 pmole of linker DNA in the presence of 6 units of T$_4$ ligase (Promega) in a standard reaction and a final volume of 20 µl at 16° C. overnight. The unidirectional linker DNA carrying a T 3'-overhang at one end was the product of annealing equal molarities of two oligonucleotides (L+2: ACAACCA-CACAACAAAC and L-2: GTGGGGGTTTGTTGTGTGGTTGTT) in 40 mM Tris-HCl (pH7.5), 20 mM MgCl$_2$ and 50 mM NaCl by heating at 90° C. for 5 min and slowly cooling down to 25° C. The DNA was amplified with 2 pmoles of each L5T72 and L-2 primers in a 25 µl PCR reaction of 100 µM dNTPs, 4 mM MgSO$_4$, 10 mM Tris-HCl (pH 9.0), 5 mM KCl, 0.1% Triton X-100 and 1.25 units of the enzyme. Amplification was done in a MiniCycler™ (MJ Research Inc., Watertown, Mass.) for 20 cycles of: 94° C., 1 min; 55° C., 2 min; and 70° C., 2 min plus 2 sec/cycle. Primer L5T722 (TGCCATTTTTGTTTTTAGTTTCTT) was labelled at 3'-ends with T$_4$ polynucleotide kinase as above. For the second amplification step, 25 µl of PCR reaction solution (as above) containing about 6×10$^6$ cpm of labelled L5T722 (about 3 pmoles) and 1.25 units of the enzyme was added to the above PCR products. Amplification was performed for 10 cycles of: 94° C., 1 min; 58° C., 2 min and 70° C, 5 min. The PCR products were ethanol precipitated, washed with 70% ethanol, dissolved in 6 µl of sequencing dye and loaded onto a 7% polyacrylamide gel as above.

REFERENCES

Anderberg, R. J., and Walker-Simmons, M. K. (1992) *Proc. Natl. Acad. Sci. U.S.A.* 89:10183–10187.

Arndt, K. T., Styles, C., Fink, G. R. (1987) *Science* 237: 874–880.

Bergman, L. W., McClinton, D. C., Madden, S. L., Preis, L. H. (1986) *Proc. Natl. Acad. Sci. U.S.A.* 83: 6070–6074.

Bieleski, R. L. (1973) *Annu. Rev. Plant. Physiol.* 24:225–252.

Boy-Marcotte, E., Garreau, H., Jacquet, M. (1987) *Yeast* 3: 85–93.

Chappell, J., Hahlbrock, K. (1984) *Nature* 311: 76–78.

Delegeane, A., Ferland, L., Mellon, P. L. (1987) *Mol. Cell Biol.* 7:3994–4002.

Deryckere, F., Gannon, F. (1994) *Biotech* 16: 405.

Dynan, W. S. (1983) *Trends Genet* 2: 196–197.

Fascher, K-D., Schmid, A., Horz, W. (1990) *EMBO J.* 9: 2523–2528.

Fife, C. A. et al. (1990) *Can. J. Bot.* 68:1840–1847.

Foster, R., Gasch, A., Kay, S., Chua, N-M. (1992) Analysis of Protein/DNA Interactions. In. Methods in Arabidopsis Research, Koncz C, Chua N-M, Schell J (eds) World Scientific, New Jersey, U.S.A., pp. 378–392.

Goldstein, A. H., et al. (1989) *Plant Physiol.* 91:175–182.

Hawkesford, M. J. and Belcher, A. R. (1991) *Planta* 185:323–329.

Kasahara, N., et al. (1991) *J. Bacteriol.* 173: 549–558.

Kieber, J. J., et al. (1993) *Cell* 72:427–441.

Kimura, S., et al. (1989) Regulation of the phosphate regulon of *Escherichia coli*: Characterization of the promoter of the pstS gene. *Mol. Gen. Genet.* 215:374–380.

Klein, C., Struhl, K. (1994) *Science* 266:280–282.

Lefebvre, D. D. and Glass, A. D. M. (1982) *Physiologia Plantarum* 54:199–206.

Makino, K., et al. (1988) *J. Mol. Biol.* 203: 85–95.

Makino, K., et al. (1991) *J. Bacteriol.* 173: 2665–2672.

Malboobi, M. A., Lefebvre, D. D. (1995) *Plant Mol. Biol.* 28:859–870.

Malboobi, M. A., Lefebvre, D. D. (1997) *Plant Mol. Biol.*, in press.

Malboobi, M. A., Tremblay, L., Lefebvre, D. D. (1996) Identification and nucleotide sequences of cDNA clones of phosphate-starvation inducible β-glucosidase genes of Brassicaceae (Accession Nos. U72153 and U72154) (PGR96–114) *Plant Physiol.* 112:1399.

Mason, H. S., et al. (1993) *Plant Cell* 5:241–251.

Matsumoto, R., et al. (1984) *Genetics* 108:53–66.

Molina, C. A., et al (1993) *Cell* 75:875–886.

McCormick, A., et al. (1990) *Nature* 345:829–832.

Nakao, J., et al. (1986) *Mol. Cell. Biol.* 6:2613–2623.

Rudolph, H., Hinnen, A. (1987) *Proc. Natl. Acad. Sci. USA* 84:1340–1344.

Sadka, A., et al. (1994) *Plant Cell* 6:737–749.

Saghai-Maroof, et al. (1984) *Proc. Natl. Acad. Sci. USA* 81: 8014–8018.

Salisbury, F. B. and Ross, C. W. (1985) *Plant Physiology* (3rd ed.), Wadsworth Publishing Co., Belmont, Calif., pp. 96–113.

Sambrook, J., et al. (1989) *Molecular Cloning—A Laboratory Manual*, 2nd Ed., Cold Spring Harbor Laboratory Press, Cold Spring Harbor, N.Y.

Sengstag, C., Hinnen, A. (1988) *Gene* 67:223–228.

Somssich, I. E., et al. (1989) *Plant Mol. Biol.* 12:227–234.

Svaren, J., et al. (1994) *EMBO J.* 13:4856–4862.

Tantikanjana, T. et al. (1993) *Plant Cell* 5:657–666.

Tommassen, J., et al. (1987) *J. Mol. Biol.* 198:633–641.

Venter, U., et al. (1994) *EMBO J.* 13:4848–4855.

Vogel, K., et al. (1989) *Mol. Cell Biol.* 9:2050–2057.

Wanner, B. L. (1993) *J. Cell Biochem.* 51:47–54.

Willmitzer, L., Wanger, K. G. (1981) *Exp. Cell Res.* 135:69–77.

Winans S C (1990) *J. Bacteriol.* 172:2433–2438.

Zhang, R., Walker, J. C. (1993) *Plant Mol. Biol.* 21:1171–1174.

EQUIVALENTS

Those skilled in the art will recognize, or be able to ascertain using no more than routine experimentation, many equivalents to the specific embodiments of the invention described herein. Such equivalents are intended to be encompassed in the scope of the following claims.

We claim:

1. A plant comprising a plant cell comprising a vector comprising isolated DNA which, when operably linked to a structural gene, induces transcription of the structural gene in a cell derived from a photosynthetic organism under conditions of phosphate deficiency but not under conditions of phosphate sufficiency.

2. Seed of a plant according to claim 1.

3. A plant part of a plant according to claim 1.

4. A tissue culture of the plant or a plant part according to claim 3.

5. A plant regenerated from a plant cell or tissue culture expressing a gene product, the plant cell or tissue culture transformed by the method of:

a) transforming the plant cell with a DNA construct comprising:

i) a phosphate-deficiency inducible promoter or a functional portion thereof, which induces transcription of a structural gene under phosphate-deficient conditions;

ii) DNA encoding a structural gene operably linked to the promoter; and iii) a 3' untranslated region containing a polyadenylated region;

b) regenerating a plant or tissue culture from the cell; and c) placing the plant or tissue culture under conditions of phosphate deficiency;

wherein the promoter induces transcription of the structural gene so that the gene product is expressed.

6. A method of transforming a plant cell, the method comprising:

(a) introducing into a plant cell:

(i) a first isolated nucleic acid from a plant which, when operably linked to a structural gene, induces transcription of the structural gene in a cell of a photosynthetic organism under conditions of phosphate deficiency but not under conditions of phosphate sufficiency; and (ii) a second isolated nucleic acid, operably linked for expression to the isolated nucleic acid of (i); and (b) selecting a transformed plant cell wherein expression of the second isolated nucleic acid occurs under conditions of phosphate deficiency but not under conditions of phosphate sufficiency.

7. The method of claim 6, wherein the first nucleic acid has the sequence of nucleotide 1 to nucleotide 1699 of SEQ ID NO:1, or at least 70% identity thereto, provided that said first nucleic acid, when transformed into a plant cell by the method of claim 6, confers onto the plant cell expression of the second isolated nucleic acid under conditions of phosphate deficiency but not under conditions of phosphate sufficiency.

8. A plant cell, transformed by the method of claim 6.

9. The method of claim 6, wherein the first nucleic acid comprises 50 to 200 or more consecutive nucleotides of nucleotide 1 to nucleotide 1699 of SEQ ID NO:1, provided that said first nucleic acid, when transformed into a plant cell by the method of claim 6, confers onto the plant cell expression of the second isolated nucleic acid under conditions of phosphate deficiency but not under conditions of phosphate sufficiency.

10. A plant cell descended from the plant cell of claim 8, provided that said first nucleic acid confers onto the plant cell expression of the second isolated nucleic acid under conditions of phosphate deficiency but not under conditions of phosphate sufficiency.

11. A plant, plant part or tissue culture, containing the plant cell of claim 10.

12. A plant, regenerated from the plant cell of claim 10.

13. A seed of the plant of claim 12.

14. A process for producing a protein or polypeptide in a plant cell, the process comprising:

(a) introducing into a plant cell:
(i) a first isolated nucleic acid from a plant which, when operably linked to a structural gene, induces transcription of the structural gene in a cell of a photosynthetic organism under conditions of phosphate deficiency but not under conditions of phosphate sufficiency; and
(ii) a second isolated nucleic acid, said second isolated nucleic acid encoding the protein or polypeptide, and said second isolated nucleic acid operably linked for expression to the isolated nucleic acid of (i);

(b) selecting a transformed plant cell wherein expression of the second isolated nucleic acid occurs under conditions of phosphate deficiency but not under conditions of phosphate sufficiency; and (c) growing the transformed plant cell under conditions of phosphate deficiency, thereby inducing transcription of the structural gene, thereby producing the protein or polypeptide in a plant cell.

15. The process of claim 14, where the protein or polypeptide is released by the plant cell, and is subsequently isolated.

16. The process of claim 15, wherein the protein or polypeptide has nutritional value to humans.

17. The process of claim 15, wherein the protein or polypeptide is a pharmaceutical.

18. The process of claim 17, wherein the protein or polypeptide is an antibody.

19. A process for producing a plant wholly or partially resistant to an external stress, the process comprising:

(a) introducing into a plant cell:
(i) a first isolated nucleic acid from a plant which, when operably linked to a structural gene, induces transcription of the structural gene in a cell of a photosynthetic organism under conditions of phosphate deficiency but not under conditions of phosphate sufficiency; and
(ii) a second isolated nucleic acid, said second isolated nucleic acid encoding a protein or polypeptide that confers resistance to the external stress, or which in turn allows the production or increased production of a substance that confers resistance to the external stress; and said second isolated nucleic acid operably linked for expression to the isolated nucleic acid of (i);

(b) selecting a transformed plant cell wherein expression of the second isolated nucleic acid occurs under conditions of phosphate deficiency but not under conditions of phosphate sufficiency; and (c) growing the transformed plant cell into a plant in which said first nucleic acid induces the expression of the second isolated nucleic acid under conditions of phosphate deficiency but not under conditions of phosphate sufficiency.

20. The process of claim 19, wherein the second isolated nucleic acid encodes a substance that confers resistance to attack by one or more of the following: insect attack, bacterial attack, fungal attack, nematode attack.

21. A method for detecting transformation in a plant cell, the method comprising:

(a) introducing into a plant cell:
(i) a first isolated nucleic acid from a plant which, when operably linked to a structural gene, induces transcription of the structural gene in a cell of a photosynthetic organism under conditions of phosphate deficiency but not under conditions of phosphate sufficiency; and
(ii) a second isolated nucleic acid which comprises the β-glucuronidase (GUS) gene and which is operably linked for expression to the isolated nucleic acid of (i); and (b) growing the transformed plant cell under conditions of phosphate deficiency, thereby inducing transcription of the second isolated nucleic acid; and (c) selecting by color change, a transformed plant cell wherein expression of the second isolated nucleic acid occurs under conditions of phosphate deficiency but not under conditions of phosphate sufficiency.

22. A plant cell transformed by the method of claim 21.

23. The method of claim 21, further comprising introducing into the plant cell a third nucleic acid encoding a structural gene and operably linked for expression to the isolated nucleic acid of (i).

24. A plant, plant part or tissue culture regenerated from the plant cell of claim 22.

25. A process for producing a substance from a plant cell or seed, wherein the amount of the substance in the plant cell or seed is increased due to the presence in the plant cell or seed of a protein or polypeptide, the process comprising:

(a) introducing into a plant cell:
(i) a first isolated nucleic acid from a plant which, when operably linked to a second isolated nucleic acid, induces transcription of the second isolated nucleic acid in a cell of a photosynthetic organism under conditions of phosphate deficiency but not under conditions of phosphate sufficiency; and (ii) a second isolated nucleic acid, said second isolated nucleic acid encoding a protein or polypeptide, and said second isolated nucleic acid operably linked for expression to the first isolated nucleic acid, and where the amount of substance in a plant cell or seed is increased due to the presence of the protein or polypeptide in the plant cell or seed;

(b) selecting a transformed plant cell wherein expression of the second isolated nucleic acid occurs under conditions of phosphate deficiency but not under conditions of phosphate sufficiency;

(c) growing the transformed plant cell or a plant regenerated therefrom under conditions of phosphate deficiency, thereby inducing transcription of the second isolated nucleic acid; and (d) isolating the substance from the transformed plant cell or a seed produced by the plant of step (c);

thereby producing the substance from the plant cell or seed.

26. The process of claim 25, wherein the substance is a protein.

27. The process of claim 25, wherein the substance is a pharmaceutical.

28. The process of claim 26, wherein the substance has nutritional value to humans.

29. The process of claim 27, wherein the substance is an antibody.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 1980 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:1:

```
AAAAACATGT TATTTTAAAT TTCCAATTTT ACTTTTCAAA TAAACTTCCA CGTTTATTCT      60
TTAATTTAAT TATTCAATTT GTTTAAATTA ACACTCACTC TGATCATTAT ATAGGATATT     120
TCAGAGATTT ATTTAGGATG TTTTACTAAT ATCAATGCAA TTTTTAAATA TATTTTATTT     180
GATTATTTGA CTATTGGGTT TGTATTTTGT ATTTTTAATA TCAAGAGAAC AAATTTTATA     240
ATTAAAAATA AATTTCTTAA AGTGTGTGTT TTAATCTAAA ACATCATATA ATTTGAAATA     300
GAGGAAATAT CATCTAATAA AGTAATGTAT ATTTGTATAG TTAATGATTT GTCTTTTTAT     360
TCGCGCAAAA TGTGTCAATT ATAAAATATA AAGAGGATAT AATTTAGTTT AGAGTTTTAG     420
ACACGAGGAC TATATATTGG AAAACAAAAA AGTAATGTAA ACCATATAGA TCATGGAATG     480
AGTCATCCTA TTAAACAGTT GTATTATATA TTTATATTTT AGTCACTAAC ACATTAATAA     540
CTTAACGTCC ATAACAAAAT AAGATCCAAA ACTCGATCTA GATCTATACG AGGCACTAAA     600
TGATCCATTG ACTTAGGGCC GGCCGATTGG TTCGAGGACT CCTCATGCTG TAAACTTTTT     660
TTTTGGACAT ACATGATATA TTTTTAAGTC ACGTTTTTAT ATTATATGTT CCACGCCCAA     720
TATAATATGT TCCAAACTAG GAAAAATAAG TAAGAATTAG TCAATGATCG AGATAATGCA     780
ATGAATCATC CTATTTATTA AATAGATTTA CTAAACTATA TATAATACAA TGATCGAGAT     840
CGTGCCATGA AGCATCCTAT ATACTATAAA AATAGTCTTA CTAAATACAT ACTCATATAG     900
TTTAGTCATT CATTAGTCCA AACATTAAAT GAGAGATCCT TTACTTGCTA CCTGAATTTT     960
TTCAGAATAA GGTATAACTT TTTTTCGAAT TAGAAACTGA TTTATGAAAG ATTAAGAGTA    1020
ATGTTCGTTA AACAAGTTAA AAAATATGTT TTTACAATTA AGTTTTGAAA ATAATAAAG     1080
TCTCCAATTA TTTGAGTATC AAAAATAGGC TTGTTATTAT TTAGGGTTTT CGTTGGTTTA    1140
AATGCAACGG GGTGTGGTTG TCATTGTGGA AGTTAATGGA AGTAATTGGT TGAGGTTTTA    1200
AACGTTATCG GACATTTTAA ATGACTGGTT TACAGTTAAA AATATGTGTA TTTACGGCAA    1260
TTTTATGATT GGCTTAGCAG TAGATGCGAC AGTGGTTTAA ACCAAAAATT ACCAAATAAA    1320
TAATATACAA TTATTAAATT ATATAAAACA CCAATATTAT ATATTTATAT ATATATGAAC    1380
ATAGTTAATT ATCGAAACCA TAGACAAAGT ACATAAGAGT TATTCCGAAA AAGGTTTATT    1440
ATGAAACACA AATAATCATA TTGGGAGATT ATGATATCCA AAATGGACTA ATCAAATAAT    1500
TAAATCCAAA ATGGATGAAG AACTTATATT AGTTCCACGC ACAATATAAT ATGTTCCAAA    1560
CTAAGTAAGA ACACAACGGT CGAGGTCATG CAATGAATCA TCCTATATAT AAAATAGTTT    1620
TACTAAACAA TTATATTTTA GTCACTCGTT AACAAACAAT CAAATCGCT ATATAAAGAA    1680
CTCCGATTGG ATGTAAACAA ATCATCATAA ACTTGTTCTC TTCCAGAAGA AACTAAAAAC    1740
AAAAATGGCA TTGCAAAAGT TTCCTCTCAT GGGGCTGCTT TTGCTCCTAA CCATCCTCGT    1800
```

```
CTCTGTGACA ACAGCGGTTG ATGATCCTGT TTGCCCGGCG ACTTCCAAGC TAAGCCGAGC    1860

AAGTTTCCCT AATGGGTTTT TGTTTGGCAC GGCTACTGCT GCGTTTCAGG TACAACAGAT    1920

TTACTAAATC ATAGTTCAAA AAACAAAAAG TAGTGTCGTT ATTGTGTTTC TATCTGAATT    1980
```

(2) INFORMATION FOR SEQ ID NO:2:

(i) SEQUENCE CHARACTERISTICS:
        (A) LENGTH: 780 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

```
AACGTTATCG GACATTTTAA ATGACTGGTT TACAGTTAAA AATATGTGTA TTTACGGCAA      60

TTTTATGATT GGCTTAGCAG TAGATGCGAC AGTGGTTTAA ACCAAAAATT ACCAAATAAA     120

TAATATACAA TTATTAAATT ATATAAAACA CCAATATTAT ATATTTATAT ATATATGAAC     180

ATAGTTAATT ATCGAAACCA TAGACAAAGT ACATAAGAGT TATTCCGAAA AAGGTTTATT     240

ATGAAACACA ATAATCATA TTGGGAGATT ATGATATCCA AAATGGACTA ATCAAATAAT      300

TAAATCCAAA ATGGATGAAG AACTTATATT AGTTCCACGC ACAATATAAT ATGTTCCAAA     360

CTAAGTAAGA ACACAACGGT CGAGGTCATG CAATGAATCA TCCTATATAT AAAATAGTTT     420

TACTAAACAA TTATATTTTA GTCACTCGTT AACAAACAAT CAAAATCGCT ATATAAAGAA     480

CTCCGATTGG ATGTAAACAA ATCATCATAA ACTTGTTCTC TTCCAGAAGA AACTAAAAAC     540

AAAAATGGCA TTGCAAAAGT TTCCTCTCAT GGGGCTGCTT TTGCTCCTAA CCATCCTCGT     600

CTCTGTGACA ACAGCGGTTG ATGATCCTGT TTGCCCGGCG ACTTCCAAGC TAAGCCGAGC     660

AAGTTTCCCT AATGGGTTTT TGTTTGGCAC GGCTACTGCT GCGTTTCAGG TACAACAGAT     720

TTACTAAATC ATAGTTCAAA AAACAAAAAG TAGTGTCGTT ATTGTGTTTC TATCTGAATT     780
```

(2) INFORMATION FOR SEQ ID NO:3:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GTACCACAGT CCAAAATAAA TGTTCCAAAC TAGCAAGCAT ATGTAAGA                   48
```

(2) INFORMATION FOR SEQ ID NO:4:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CTGCACAAAT G                                                           11
```

(2) INFORMATION FOR SEQ ID NO:5:

```
        (i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: peptide (xi) SEQUENCE DESCRIPTION: SEQ ID NO:5:

AGCAAAAGCA GCCCCATGAG AGGAA                                              25

(2) INFORMATION FOR SEQ ID NO:6:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: peptide (xi) SEQUENCE DESCRIPTION: SEQ ID NO:6:

ACAACCACAC AACAAAC                                                       17

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: peptide (xi) SEQUENCE DESCRIPTION: SEQ ID NO:7:

GTGGGGGTTT GTTGTGTGGT TGTT                                               24

(2) INFORMATION FOR SEQ ID NO:8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: peptide (xi) SEQUENCE DESCRIPTION: SEQ ID NO:8:

TGCCATTTTT GTTTTTAGTT TCTT                                               24
```